United States Patent
Christensen et al.

(10) Patent No.: US 10,472,414 B2
(45) Date of Patent: Nov. 12, 2019

(54) ANTIBODIES SPECIFIC TO PYROGLUTAMATED Aβ

(71) Applicant: H. Lundbeck A/S, Valby (DK)

(72) Inventors: Søren Christensen, Jyllinge (DK); Lone Helboe, Frederiksberg (DK)

(73) Assignee: H. Lundbeck A/S, Valby (DK)

( * ) Notice: Subject to any disclaimer, the term of this patent is extended or adjusted under 35 U.S.C. 154(b) by 243 days.

(21) Appl. No.: 15/288,476

(22) Filed: Oct. 7, 2016

(65) Prior Publication Data

US 2017/0022268 A1    Jan. 26, 2017

Related U.S. Application Data

(63) Continuation of application No. 14/009,492, filed as application No. PCT/EP2012/055598 on Mar. 29, 2012, now Pat. No. 9,499,610.

(60) Provisional application No. 61/473,178, filed on Apr. 8, 2011.

(30) Foreign Application Priority Data

Apr. 8, 2011    (DK) ................................ 2011 00275

(51) Int. Cl.
| | | |
|---|---|---|
| C07K 16/00 | (2006.01) | |
| C12P 21/08 | (2006.01) | |
| A61K 39/395 | (2006.01) | |
| A61K 39/40 | (2006.01) | |
| C07K 16/18 | (2006.01) | |
| A61K 39/00 | (2006.01) | |
| G01N 33/68 | (2006.01) | |
| C07K 1/00 | (2006.01) | |

(52) U.S. Cl.
CPC .......... *C07K 16/18* (2013.01); *A61K 39/0007* (2013.01); *G01N 33/6896* (2013.01); *A61K 2039/575* (2013.01); *C07K 2317/33* (2013.01); *C07K 2317/34* (2013.01); *C07K 2317/56* (2013.01); *C07K 2317/565* (2013.01); *C07K 2317/70* (2013.01); *C07K 2317/92* (2013.01); *G01N 2333/4709* (2013.01); *G01N 2800/2821* (2013.01)

(58) Field of Classification Search
None
See application file for complete search history.

(56) References Cited

U.S. PATENT DOCUMENTS 7,122,374 B1    10/2006    Saido et al.

FOREIGN PATENT DOCUMENTS

| DK | PA 201100275 | 3/2012 |
|---|---|---|
| WO | WO 2004/013172 | 2/2004 |
| WO | WO 2010/009987 | 1/2010 |
| WO | WO 2010/129276 | 11/2010 |
| WO | WO 2012/021469 | 2/2012 |
| WO | WO 2012/136552 | 10/2012 |

OTHER PUBLICATIONS

Janeway et al., Immunology Third Edition, Garland Publishing Inc., Chapter 3, Structure of the Antibody Molecule and Immunoglobulin Genes, pp. 3:1-3:11. (Year: 1997).*
Rudikoff et al. PNAS, vol. 79 p. 1979-1983 (Year: 1982).*
Casset et al. BBRC(2003) 307, 198-205. (Year: 2003).*
Acero, G. et al. (2009) "Immunodominant Epitope and Properties of Pyroglutamate-Modified Aβ-Specific Antibodies Produced in Rabbits," J. Neuroimmunol. 213:39-46.
Casset, F. et al. (2003) "A Peptide Mimetic of an Anti-CD4 Monoclonal Antibody by Rational Design," Biochem. Biophys. Res. Commun. 307:198-205.
Colman, P.M. et al. (1994) "Effects of Amino Acid Sequence Changes on Antibody-Antigen Interactions," Res. Immunology 145:33-36.
International Search Report PCT/EP2012/055598 (WO 2012/136552) (dated 2012) (8 pages).
Janeway et al. (1997) "Chapter 3: Structure of the Antibody Molecule and Immunoglobulin Genes," Immunology Third Edition pp. 3:1-3:11.
Paul, W.E. (1993) Fundamental Immunology $3^{rd}$ Ed., p. 242.
Portolano et al. (1993) "Lack of Promiscuity in Autoantigen-Specific H and L Chain Combination as Revealed by Human H and L Chain "Roulette"," J. Immunology 150:880-887.
Rudikoff, S. et al. (1982) "Single Amino Acid Substitution Altering Antigen-Binding Specificity," PNAS 79:1979-1983.
Saido, T.C. et al. (1995) "Dominant and Differential Deposition of Distinct β-Amyloid Peptide Species AβN3(pE), in Senile Plaques," Neuron 14:457-466.
Shi, Q. et al. (2010) "Intra-Cerebral Injection of AβN3pE Antibody Reduces Aβ Deposits in 3xTg AD Mice,": Society for Neurosci. Abstract Viewer and Itinerary Planner 40: Abstract 650.
Wirths, O. et al. (2009) "Intraneuronal Pyroglutamate-Abeta 3-42 Triggers Neurodegeneration and Methal Neurological Deficits in a Transgenic Mouse Model," Acta Neuropathol. 118:487-496.
Wirths, O. et al. (2010) "Identification of Low Molecular Weight Pyroglutamate Abeta Oligomers in Alzheimer Disease," J. Biol. Chem 285(53):41517-41524.
Wirths, O. et al. (2010) "Pyroglutamate Abeta Pathology in APP/PS1KI Mice, Sporadic and Familial Alzheimer's Disease Cases," J. Neural. Transmission 117:85-96.
Written Opinion of the International Searching Authority for Application No. PCT/EP2012/055598 dated Jul. 2, 2012 (11 pages).

\* cited by examiner

*Primary Examiner* — Chun W Dahle

(74) *Attorney, Agent, or Firm* — Wolf, Greenfield & Sacks, P.C.

(57) ABSTRACT

The present invention relates to antibodies specific for pyroglutamated Aβ, as well as their use in the treatment of Alzheimer's disease and as use in diagnostic methods or as diagnostic imaging ligands. Further, is provided pyroglutamated N-terminal fragments of murine or human Aβ to generate antibodies and for use in therapeutic purposes.

12 Claims, 4 Drawing Sheets

Specification includes a Sequence Listing.

| Clone | Isotype Type (mouse) | Ka₁ (1/M) | Kd₁ (1/s) | KD₁ (M) | Ka₂ (1/RUs) | Kd₂ (1/s) | KD₂ (RU) | KD (M) |
|---|---|---|---|---|---|---|---|---|
| LuAb1h | IgG1, κ | 3,64e4 | 4,22e-6 | 1,16e-10 | 1,32e-4 | 9,43e-3 | 71,4 | 8,2e-9 |
| LUAb2h | IgG2a, κ | 1,35e5 | 4,64e-4 | 3,46e-9 | 5,94e-2 | 1,1 | 18,52 | 64e-9 |

Fig. 1A

| Clone | Isotype Type (mouse) | Ka₁ (1/M) | Kd₁ (1/s) | KD₁ (M) | Ka₂ (1/RUs) | Kd₂ (1/s) | KD₂ (RU) | KD (M) |
|---|---|---|---|---|---|---|---|---|
| LuAb1m | IgG1, κ | 3,04e5 | 5,03e-3 | 1,65e-8 | 1,57 | 5,6 | 3,57 | 58,9e-9 |
| LuAb2m | IgG1, κ | 5,06e5 | 7,5e-3 | 1,48e-8 | 0,0155 | 0,0676 | 4,36 | 64,6e-9 |

ANTIBODIES SPECIFIC TO PYROGLUTAMATED Aβ

CROSS-REFERENCE TO RELATED APPLICATIONS

This application is a continuation of, and claims priority to, U.S. patent application Ser. No. 14/009,492, (filed on Oct. 11, 2013; patented), which application is a § 371 application of US Patent Application Serial No. PCT/EP2012/055598 (filed on Mar. 29, 2012; now lapsed), which claims priority to U.S. Patent Application Ser. No. 61/473,178 (filed on Apr. 8, 2011) and and Denmark Application PA201100275 having a filing date of Apr. 8, 2011, each of which applications is herein incorporated by reference in its entirety.

FIELD OF THE INVENTION

The present invention relates to antibodies specific for pyroglutamated Aβ, as well as their use in the treatment of Alzheimer's disease and as use in diagnostic methods or as diagnostic imaging ligands. Further, is provided pyroglutamated N-terminal fragments of murine or human Aβ to generate antibodies and for use in therapeutic purposes.

REFERENCE TO SEQUENCE LISTING

This application includes one or more Sequence Listings pursuant to 37 C.F.R. 1.821 et seq., which are disclosed in computer-readable media (file name: 1275_0020C2_ST25.txt, created on Oct. 6, 2016, and having a size of 28,472 bytes), which file is herein incorporated by reference in its entirety.

BACKGROUND OF THE INVENTION

Alzheimer disease (AD) is characterised by a progressive dementia occurring in mid or late life. The first events leading to AD are believed to occur some 10 to 20 years before the cognitive symptoms appear, and evidence suggests that a key event in the pathology of AD is the deposit of extracellular aggregated amyloid β (Aβ) plaques in the brain. Aβ is generated by proteolytic cleavage from the amyloid precursor protein (APP) which is a large transmembrane protein with a suggested neutrophic function. The main Aβ variants observed in the human brain are Aβ 1-40 and Aβ 1-42, but also truncated N-terminal variants and other modified species thereof are observed in the plaques.

Immunotherapy against the Aβ plaques has been shown to disrupt the Aβ aggregates and promote the clearance of plaques in the brain. Both active immunogenic approaches with Aβ or fragments thereof as well as passive immunisation using anti-Aβ antibodies have proven effective in different animal models. Vaccination of humans with Aβ was shown to prevent the development of Aβ plaques and reduce the Aβ burden in patients in a clinical study, however the study was stopped due to inflammation in the brain of some of the patients. An immunogenic strategy to reduce the amyloid plaques thus relies on a delicate balance of activating the immune system but still avoiding an uncontrollable inflammation to occur (Monsonego et al (2003) *J clin invest* 112, 415-422). This requires a precise knowledge of the chemical nature of inter alia the nature of the deposit. In an attempt to understand the exact composition of the amyloid plaques one of the most abundant N-truncated Aβ peptides identified are carrying a pyroglutamate at position 3 ("AβpE3," N-terminally truncated Aβ starting with pyroglutamate) (Saido et al. (1996) *Neuron* 14, 457-466). These pyroglutamated peptides have been shown to accumulate in plaques as well as around the blood vessels in AD, and due to its hydrophobic potential it has been shown that these peptides increase the aggregation. A recent transgenic mouse model expressing AβpE3-42 in neurons demonstrates that this peptide is neurotoxic in vivo and leads to loss of neurons (Wirths et al. (2009) *Acta Neuropathol* 118, 487-496).

Antibodies with specificities against the N-terminal pyroglutamate are believed to be advantageous because of their specificity towards only the pathogenic pyroglutamate N-terminal species of Aβ, thereby leaving APP or other cross reacting species untouched. It is thus envisaged that the risk of uncontrollable cerebral inflammation will be reduced compared to antibodies directed to non-pyroglutamated Aβ or fragments thereof.

Antibodies targeting AβpE3 peptides and aggregates have been made (Acero et al (2009) *J Neuroimmunol* 213, 39-46; Saido et al. (1996) *Neuron* 14, 457-466; and U.S. Pat. No. 7,122,374) and identification of various AβpE fragments have been hypothesized as epitopes (WO2004/013172; WO2010/009987; WO2010/129276; and Wirths et al. (2010) *J Biol Chem* 285(53), 41517-24, Epub 2010 Oct. 22).

The present invention provides two highly specific monoclonal antibodies directed against human AβpE3 (5C9 and 2E83, respectively) as well as two highly specific monoclonal antibodies directed against murine AβpE3 (2E4 and 1G11, respectively).

SUMMARY OF THE INVENTION

The invention relates to an antibody, in particular an isolated antibody, or a fragment thereof, specific for human AβpE3 which antibody comprises, or consists, of:
  a heavy chain variable region ($V_H$) CDR1 comprising GYTFTDYYX$_1$N (SEQ ID NO:56),
  a heavy chain variable region ($V_H$) CDR2 comprising WX$_2$X$_3$PGSGNX$_4$KYNEKFKG (SEQ ID NO:57),
  a heavy chain variable region ($V_H$) CDR3 comprising EGX$_5$X$_6$X$_7$Y (SEQ ID NO:58),
  a light chain variable region ($V_L$) CDR1 comprising KSSQSLLX$_8$SNGX$_9$X$_{10}$YLN (SEQ ID NO:59),
  a light chain variable region ($V_L$) CDR2 comprising X$_{11}$VSKLDS (SEQ ID NO:60), and
  a light chain variable region ($V_L$) CDR3 comprising VQGTHX$_{12}$PFT (SEQ ID NO:61);
  wherein X$_1$ to X$_{12}$ symbolizes a natural amino acid.

The invention further relates to an antibody, in particular an isolated antibody, or a fragment thereof, specific for murine AβpE3 which antibody comprises, or consists, of:
  a heavy chain variable region ($V_H$) CDR1 comprising GX$_1$TLX$_2$DAWMX$_3$ (SEQ ID NO:62),
  a heavy chain variable region ($V_H$) CDR2 comprising EIRX$_4$KAX$_5$X$_6$HATX$_7$YAESVKG (SEQ ID NO:63),
  a heavy chain variable region ($V_H$) CDR3 comprising HX$_8$X$_9$ (SEQ ID NO:64),
  a light chain variable region ($V_L$) CDR1 comprising X$_{10}$ASQGIX$_{11}$X$_{12}$X$_{13}$X$_{14}$G (SEQ ID NO:65),
  a light chain variable region ($V_L$) CDR2 comprising HGTKLED (SEQ ID NO:36), and
  a light chain variable region ($V_L$) CDR3 comprising VQYX$_{15}$QFPYT (SEQ ID NO:66)
  wherein X$_1$ to X$_{15}$ symbolizes a natural amino acid.

In further embodiments the invention provides four specific monoclonal antibodies as set forth in the claims, as well as their use in the treatment of Alzheimer's disease and as use in diagnostic methods or as diagnostic imaging ligands. The pyroglutamated N-terminal 3-11 amino acids of murine or human Aβ is also provided for the generation of antibodies or for use in pharmaceutical compositions.

BRIEF DESCRIPTION OF DRAWINGS

FIGS. 1A and 1B. Biacore binding of pE3-specific monoclonal antibodies (MABs) to human AβpE3 (FIG. 1A) and murine AβpE3 (FIG. 1B). Data for two monoclonal antibodies highly specific for human AβpE3, LuAb1h and LuAb2h (which are the same as 5C9 and 2E83, respectively), and two monoclonal antibodies highly specific for murine AβpE3, exemplified by LuAb1m and LuAb2m is shown.

DETAILED DESCRIPTION OF THE INVENTION

Definitions

Figure 2A:
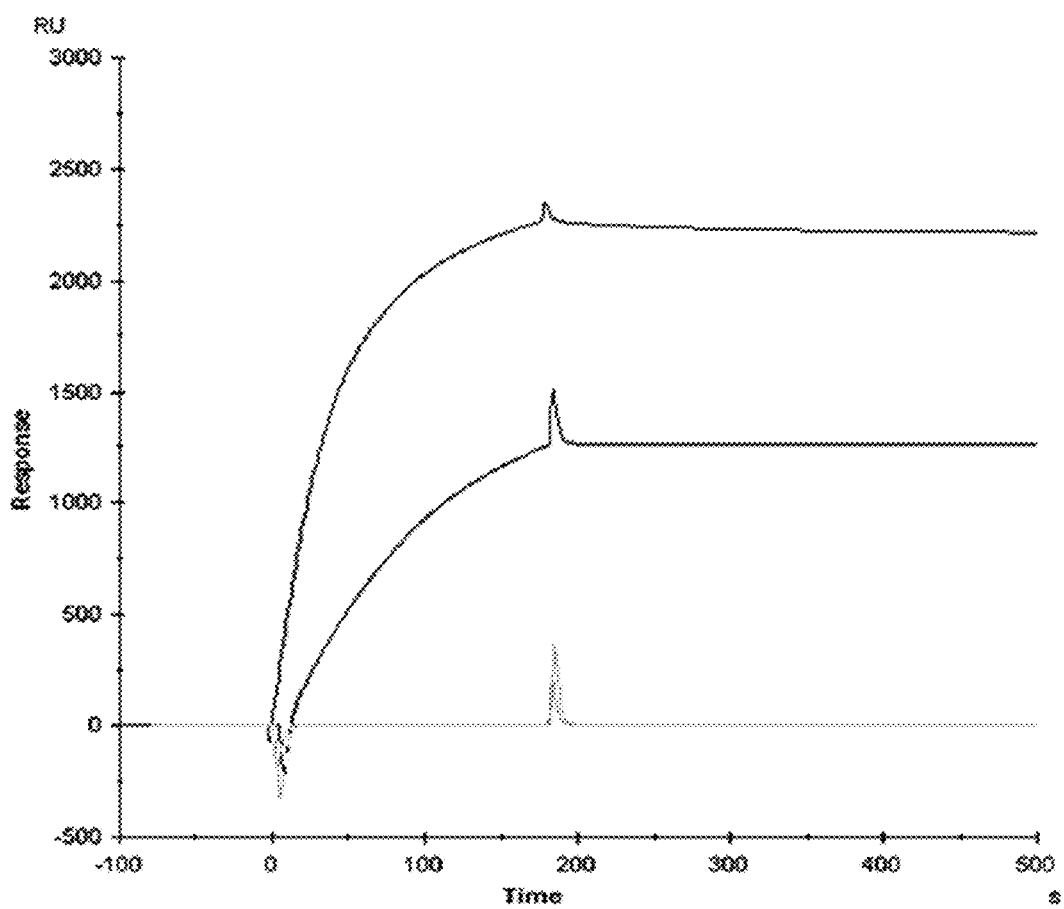
FIGS. 2A and 2B. Shows the Biacore binding curves to human AβpE3 (FIG. 2A) and murine AβpE3 (FIG. 2B) peptides for the antibodies in FIG. 1A-1B.

The terms "pyroglutamated Aβ", and "AβpE" are used interchangeably herein, and, unless specified otherwise, include any variants, isoforms and species homologs of pyroglutamated A. For example, AβpE3 refers to different Aβ variants, including, but not limited to the fragments Aβ3-42, Aβ3-40 or Aβ3-11, which are pyroglutamated at the N-terminal end specifically at the position 3 glutamic acid.

The term "immunoglobulin" refers to a class of structurally related glycoproteins consisting of two pairs of polypeptide chains, one pair of light (L) low molecular weight chains and one pair of heavy (H) chains, which may all four be inter-connected by disulfide bonds. The structure of immunoglobulins has been well characterized. See for instance Fundamental Immunology Ch. 7 (Paul, W., ed., 2nd ed. Raven Press, N.Y. (1989)). Briefly, each heavy chain typically is comprised of a heavy chain variable region (abbreviated herein as $V_H$ or VH) and a heavy chain constant region. The heavy chain constant region typically is comprised of three domains, $C_H1$, $C_H2$, and $C_H3$. Each light chain typically is comprised of a light chain variable region (abbreviated herein as $V_L$ or VL) and a light chain constant region. The light chain constant region typically is comprised of one domain, $C_L$. The $V_H$ and $V_L$ regions may be further subdivided into regions of hypervariability (or hypervariable regions which may be hypervariable in sequence and/or form of structurally defined loops), also termed complementarity determining regions (CDRs), interspersed with regions that are more conserved, termed framework regions (FRs). Each $V_H$ and $V_L$ is typically composed of three CDRs and four FRs, arranged from amino-terminus to carboxyterminus in the following order: FR1, CDR1, FR2, CDR2, FR3, CDR3, FR4 (see also Chothia and Lesk *J. Mol. Biol.* 196, 901-917 (1987)). Typically, the numbering of amino acid residues in this region is according to IMGT, Sequences of Proteins of Immunological Interest, 5th Ed. Public Health Service, National Institutes of Health, Bethesda, Md. (1991).

The term "antibody" (Ab) in the context of the present invention refers to an immunoglobulin molecule or according to some embodiments of the invention may be a fragment of an immunoglobulin molecule, or a derivative of either thereof, which has the ability to specifically bind to an antigen. The variable regions of the heavy and light chains of the immunoglobulin molecule contain a binding domain that interacts with an antigen as outlined above under "immunoglobulin". An anti-AβpE3 antibody may also be a bispecific antibody, diabody, or similar molecule (see for instance *PNAS USA* 90(14), 6444-8 (1993) for a description of diabodies). Further, it has been shown that the antigen-binding function of an antibody may be performed by fragments of a full-length antibody. Examples of binding fragments encompassed within the term "antibody" include (i) a Fab' or Fab fragment, a monovalent fragment consisting of the $V_L$, $V_N$, $C_L$ and $C_H1$ domains, or a monovalent antibody as described in WO2007059782; (ii) F(ab')$_2$ fragments, bivalent fragments comprising two Fab fragments linked by a disulfide bridge at the hinge region; (iii) a Fd fragment consisting essentially of the $V_H$ and $C_H1$ domains; (iv) a Fv fragment consisting essentially of a $V_L$ and $V_H$ domains, (v) a dAb fragment (Ward et al., *Nature* 341, 544-546 (1989)), which consists essentially of a $V_H$ domain and also called domain antibodies (Holt et al; *Trends Biotechnol.* 2003 November; 2i(II):484-90); (vi) camelid or nanobodies (Revets et al; *Expert Opin Biol Ther.* 2005 January; 5_(I): I II-24) and (vii) an isolated complementarity determining region (CDR). Furthermore, although the two domains of the Fv fragment, $V_L$ and $V_H$, are coded for by separate genes, they may be joined, using recombinant methods, by a synthetic linker that enables them to be made as a single protein chain in which the $V_L$ and $V_H$ regions pair to form monovalent molecules (known as single chain antibodies or single chain Fv (scFv), see for instance Bird et al., *Science* 242, 423-426 (1988) and Huston et al., *PNAS USA* 85, 5879-5883 (1988)). Such single chain antibodies are encompassed within the term antibody unless otherwise noted or clearly indicated by context. Although such fragments are generally included within the meaning of antibody, they collectively, and each independently, are unique features of the present invention, exhibiting different biological properties and utility. These and other useful antibody fragments in the context of the present invention are discussed further herein. It also should be understood that the term antibody, unless specified otherwise, also includes polyclonal antibodies, monoclonal antibodies (MAbs), antibody-like polypeptides, such as chimeric antibodies and humanized antibodies, and antibody fragments retaining the ability to specifically bind to the antigen (antigen-binding fragments) provided by any known technique, such as enzymatic cleavage, peptide synthesis, and recombinant techniques. An antibody as generated can possess any isotype.

An "anti-AβpE3 antibody" is an antibody as described above, which binds specifically to variant fragments of Aβ, including, but not limited to, pyroglutamated N-terminal truncated forms such as the fragments Aβ3-42, 3-40 or 3-11, which are pyroglutamated in the N-terminal end at position 3.

The term "human antibody", as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or during gene rearrangement or by somatic mutation in vivo).

The term "humanized antibody", as used herein, is intended to include antibodies in which CDR sequences are derived from the germline of another mammalian species, such as a mouse, and have been grafted onto human framework sequences. Humanized monoclonal antibodies may be generated by a hybridoma which includes a B lymphocyte cell obtained from a transgenic or transchromosomal non-human animal, such as a transgenic mouse, having a genome comprising a human heavy chain transgene and a light chain transgene, fused to an immortalized cell. For example, when non-human antibodies are prepared with respect to a particular antigen, the variable regions can be "reshaped" or "humanized" by grafting CDRs derived from nonhuman antibody on the FRs present in the human antibody to be modified. Application of this approach has been reported by Sato, K. et al. *Cancer Research* 53:851-856 (1993); Riechmann, L., et al., *Nature* 332:323-327 (1988); Verhoeyen, M., et al., *Science* 239:1534-1536 (1988); Kettleborough, C. A., et al., *Protein Engineering* 4:773-3783 (1991); Maeda, H., et al., *Human Antibodies Hybridoma* 2:124-134 (1991); Gorman, S. D., et al., *Proc Natl Acad Sci USA* 88:4181-4185 (1991); Tempest, P. R., et al., *Bio/Technology* 9:266-271 (1991); Co, M. S., et al., *Proc Natl Acad Sci USA* 88:2869-2873 (1991); Carter, P., et al., *Proc Natl Acad Sci USA* 89:4285-4289 (1992); and Co, M. S. et al., *J Immunol* 148:1149-1154 (1992). In some embodiments, humanized antibodies preserve all CDR sequences (for example, a humanized mouse antibody which contains all six CDRs from the mouse antibodies). In other embodiments, humanized antibodies have one or more CDRs (one, two, three, four, five, or six) which are altered with respect to the original antibody, which are also termed one or more CDRs "derived from" one or more CDRs from the original antibody. Humanized antibodies may refer to chimeric molecules prepared using recombinant techniques.

The terms "monoclonal antibody" or "monoclonal antibody composition" as used herein refer to a preparation of antibody molecules of single molecular composition. A monoclonal antibody composition displays a single binding specificity and affinity for a particular epitope. Accordingly, the term "mouse or murine monoclonal antibody" refers to antibodies displaying a single binding specificity which have variable and constant regions derived from murine or mouse germline immunoglobulin sequences.

As used herein, the term "binding" in the context of the binding of an antibody to a predetermined antigen typically refers to binding with an affinity corresponding to a $K_D$ of about $10^{-7}$ M or less, such as about $10^{-8}$ M or less, such as about $10^{-9}$ M or less when determined by for instance surface plasmon resonance (SPR) technology in a BIAcore 3000 instrument using the antigen as the ligand and the antibody as the analyte, and binds to the predetermined antigen with an affinity corresponding to a $K_D$ that is at least ten-fold lower, such as at least 100 fold lower, for instance at least 1,000 fold lower, such as at least 10,000 fold lower, for instance at least 100,000 fold lower than its affinity for binding to a non-specific antigen (e.g., BSA, casein) other than the predetermined antigen or a closely-related antigen. The amount with which the affinity is lower is dependent on the $K_D$ of the antibody, so that when the $K_D$ of the antibody is very low (that is, the antibody is highly specific), then the amount with which the affinity for the antigen is lower than the affinity for a non-specific antigen may be at least 10,000 fold.

The term "$k_d$" (sec$^{-1}$ or 1/s), as used herein, refers to the dissociation rate constant of a particular antibody-antigen interaction. Said value is also referred to as the $k_{off}$ value.

The term "$k_a$" (M$^{-1}$× sec$^{-1}$ or 1/M), as used herein, refers to the association rate constant of a particular antibody-antigen interaction.

The term "$K_D$" (M), as used herein, refers to the dissociation equilibrium constant of a particular antibody-antigen interaction.

The term "$K_A$" (M$^{-1}$ or 1/M), as used herein, refers to the association equilibrium constant of a particular antibody-antigen interaction and is obtained by dividing the $k_a$ by the $k_d$.

The present invention also provides antibodies comprising functional variants of the $V_L$ region, $V_H$ region, or one or more CDRs of the antibodies of the examples. A functional variant of a $V_L$, $V_H$, or CDR used in the context of an anti-AβpE3 antibody still allows the antibody to retain at least a substantial proportion (at least about 80%, 90%, 95% or more) of the affinity and/or the specificity/selectivity of the parent antibody and in some cases such an anti-AβpE3 antibody may be associated with greater affinity, selectivity and/or specificity than the parent antibody. Such functional variants typically retain significant amino acid sequence identity to the parent antibody. The percent identity between two amino acid sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences may be accomplished using a mathematical algorithm, as described in the non-limiting examples below.

The sequence of CDR variants may differ from the sequence of the CDR of the parent antibody sequences through substitutions; for instance substituted at least 10, such as at least 9, 8, 7, 6, 5, 4, 3, 2 or 1 of the amino acid residues. According to an embodiment of the invention it is furthermore envisaged that the amino acids in the CDR regions may be substituted with conservative substitutions, as defined in the below 3 tables. For example, the acidic residue Asp can be substituted with Glu without substantially affecting the binding characteristic of the antibody.

In the context of the present invention, conservative substitutions may be defined by substitutions within the classes of amino acids reflected in one or more of the following three tables:

Amino Acid Residue Classes for Conservative Substitutions:

| | |
|---|---|
| Acidic Residues | Asp (D) and Glu (E) |
| Basic Residues | Lys (K), Arg (R), and His (H) |
| Hydrophilic Uncharged Residues | Ser (S), Thr (T), Asn (N), and Gln (Q) |
| Aliphatic Uncharged Residues | Gly (G), Ala (A), Val (V), Leu (L), and Ile (I) |
| Non-polar Uncharged Residues | Cys (C), Met (M), and Pro (P) |
| Aromatic Residues | Phe (F), Tyr (Y), and Trp (W) |

Alternative Conservative Amino Acid Residue Substitution Classes:

| | | | |
|---|---|---|---|
| 1 | A | S | T |
| 2 | D | E | |

| | | | |
|---|---|---|---|
| 3 | N | Q | |
| 4 | R | K | |
| 5 | I | L | M |
| 6 | F | Y | W |

Alternative Physical and Functional Classifications of Amino Acid Residues:

| | |
|---|---|
| Alcohol group-containing residues | S and T |
| Aliphatic residues | I, L, V, and M |
| Cycloalkenyl-associated residues | F, H, W, and Y |
| Hydrophobic residues | A, C, F, G, H, 1, L, M, R, T, V, W, and Y |
| Negatively charged residues | D and E |
| Polar residues | C, D, E, H, K, N, Q, R, S, and T |
| Positively charged residues | H, K, and R |
| Small residues | A, C, D, G, N, P, S, T, and V |
| Very small residues | A, G, and S |
| Residues involved in turn formation | A, C, D, E, G, H, K, N, Q, R, S, P, and T |
| Flexible residues | Q, T, K, S, G, P, D, E, and R |

More conservative substitutions groupings include: valine-leucine-isoleucine, phenylalanine-tyrosine, lysine-arginine, alanine-valine, and asparagine-glutamine.

Additional groups of amino acids may also be formulated using the principles described in, e.g., Creighton (1984) Proteins: Structure and Molecular Properties (2d Ed. 1993), W. H. Freeman and Company.

In one embodiment of the present invention, conservation in terms of hydropathic/hydrophilic properties and residue weight/size also is substantially retained in a variant CDR as compared to a CDR of an antibody of the examples (e.g., the weight class, hydropathic score, or both of the sequences are at least about 80%, at least about 85%, at least about 90%, at least about 95%, or more retained). For example, conservative residue substitutions may also or alternatively be based on the replacement of strong or weak based weight based conservation groups, which are known in the art.

The retention of similar residues may also or alternatively be measured by a similarity score, as determined by use of a BLAST program (e.g., BLAST 2.2.8 available through the NCBI using standard settings BLOSUM62, Open Gap=I I and Extended Gap=I). Suitable variants typically exhibit at least about 80%, at least about 90%, at least about 95%, or more similarity to the parent peptide.

As used herein, "isotype" refers to the immunoglobulin class (for instance IgG1, IgG2, IgG3, IgG4, IgD, IgA, IgE, or IgM) that is encoded by heavy chain constant region genes.

The term "epitope" means an antigenic determinant capable of specific binding to an antibody. Epitopes usually consist of surface groupings of molecules such as amino acids or sugar side chains and usually have specific three dimensional structural characteristics, as well as specific charge characteristics. Conformational and nonconformational epitopes are distinguished in that the binding to the former, but not the latter, is lost in the presence of denaturing solvents. The epitope may comprise amino acid residues directly involved in the binding (also called immunodominant component of the epitope) and other amino acid residues, which are not directly involved in the binding, such as amino acid residues which are effectively blocked by the specifically antigen binding peptide (in other words, the amino acid residue is within the footprint of the specifically antigen binding peptide).

As used herein, a humanized antibody is "derived from" a particular germline sequence if the antibody is obtained from a system using human immunoglobulin sequences, for instance by immunizing a transgenic mouse carrying human immunoglobulin genes or by screening a human immunoglobulin gene library, and wherein the selected human antibody V domain sequence is at least 90%, such as at least 95%, for instance at least 96%, such as at least 97%, for instance at least 98%, or such as at least 99% identical in amino acid V domain sequence to the amino acid sequence encoded by the germline immunoglobulin gene.

Typically, outside the heavy chain, a human antibody derived from a particular human germline sequence will display no more than 20 amino acid differences, e.g. no more than 10 amino acid differences, such as no more than 9, 8, 7, 6 or 5, for instance no more than 4, 3, 2, or 1 amino acid difference from the amino acid sequence encoded by the germline immunoglobulin gene.

The term "transgenic non-human animal" refers to a non-human animal having a genome comprising one or more human heavy and/or light chain transgenes or transchromosomes (either integrated or non-integrated into the animal's natural genomic DNA) and which is capable of expressing fully human antibodies. For example, a transgenic mouse can have a human light chain transgene and either a human heavy chain transgene or human heavy chain transchromosome, such that the mouse produces human anti-AβpE3 antibody when immunized with AβpE3 antigen and/or cells expressing AβpE3. The human heavy chain transgene may be integrated into the chromosomal DNA of the mouse, as is the case for transgenic mice, for instance HuMAb mice, such as HCo7 or HCo12 mice, or the human heavy chain transgene may be maintained extrachromosomally, as is the case for transchromosomal KM mice as described in WO02/43478. Such transgenic and transchromosomal mice (collectively referred to herein as "transgenic mice") are capable of producing multiple isotypes of human monoclonal antibodies to a given antigen (such as IgG, IgA, IgM, IgD and/or IgE) by undergoing V-D-J recombination and isotype switching.

Transgenic, nonhuman animal can also be used for production of antibodies against a specific antigen by introducing genes encoding such specific antibody, for example by operatively linking the genes to a gene which is expressed in the milk of the animal.

The term "treatment" or "treating" as used herein means ameliorating, slowing or reversing the progress or severity of a disease or disorder, or ameliorating, slowing or reversing one or more symptoms or side effects of such disease or disorder. For purposes of this invention, "treatment" or "treating" further means an approach for obtaining beneficial or desired clinical results, where "beneficial or desired clinical results" include, without limitation, alleviation of a symptom, diminishment of the extent of a disorder or disease, stabilized (i.e., not worsening) disease or disorder state, delay or slowing of the progression a disease or disorder state, amelioration or palliation of a disease or disorder state, and remission of a disease or disorder, whether partial or total, detectable or undetectable.

An "effective amount", when applied to an antibody of the invention, refers to an amount sufficient, at dosages and for periods of time necessary, to achieve an intended biological effect or a desired therapeutic result including, without limitation, clinical results. The phrase "therapeutically effective amount" when applied to an antibody of the invention is intended to denote an amount of the antibody that is sufficient to ameliorate, palliate, stabilize, reverse, slow or delay the progression of a disorder or disease state, or of a symptom of the disorder or disease. In an embodiment, the method of the present invention provides for administration of the antibody in combinations with other compounds. In such instances, the "effective amount" is the amount of the combination sufficient to cause the intended biological effect.

A therapeutically effective amount of an anti-AβpE3 antibody may vary according to factors such as the disease state, age, sex, and weight of the individual, and the ability of the anti-AβpE3 antibody to elicit a desired response in the individual. A therapeutically effective amount is also one in which any toxic or detrimental effects of the antibody or antibody portion are outweighed by the therapeutically beneficial effects.

FURTHER ASPECTS OF THE INVENTION

The present invention encompasses the production of novel monoclonal antibodies with specificities for human AβpE3, particularly human AβpE3-11 peptide, relative to murine AβpE3-11 peptide. The invention provides a method for producing anti-AβpE3 monoclonal antibodies that specifically bind AβpE3 peptides, particularly human AβpE3-11, with a greater affinity than said monoclonal antibodies bind murine AβpE3-11, said method comprising: (a) immunizing one or more mice with purified human AβpE3-11-C peptide; (b) producing hybridoma cell lines from spleen cells of said one or more mice; (c) screening said hybridoma cell lines for one or more hybridoma cell lines that produce antibodies that specifically bind human AβpE3-11, with a greater affinity than said monoclonal antibodies bind murine AβpE3-11.

Comparison between antibodies specific for human and murine AβpE3, particularly the AβpE3-11 peptide, revealed substantial conservation among several of the amino acids in the CDR regions as well as positions that allows different types of amino acid replacements.

| Clone | Specific for | $V_H$ CDR1 | $V_H$ CDR2 | $V_H$ CDR3 |
|---|---|---|---|---|
| 5C9 | Human AβpE3-11 | GYTFTDYYLN (SEQ ID NO: 12) | WIYPGSGNVKYNEKFKG (SEQ ID NO: 13) | EGLIVY (SEQ ID NO: 14) |
| 2E8 | Human AβpE3-11 | GYTFTDYYIN (SEQ ID NO: 18) | WLNPGSGNTKYNEKFKG (SEQ ID NO: 19) | EGIPDY (SEQ ID NO: 20) |
| Difference | | GYTFTDYYXN (SEQ ID NO: 44) | WXXPGSGNXKYNEKFKG (SEQ ID NO: 45) | EGXXXY (SEQ ID NO: 46) |
| | | $V_L$ CDR1 | $V_L$ CDR2 | $V_L$ CDR3 |
| 5C9 | Human AβpE3-11 | KSSQSLLHSNGESYLN (SEQ ID NO: 15) | AVSKLDS (SEQ ID NO: 16) | VQGTHFPFT (SEQ ID NO: 17) |
| 2E8 | Human AβpE3-11 | KSSQSLLYSNGKTYLN (SEQ ID NO: 21) | VVSKLDS (SEQ ID NO: 22) | VQGTHYPFT (SEQ ID NO: 23) |
| Difference | | KSSQSLLXSNGXXYLN (SEQ ID NO: 47) | XVSKLDS (SEQ ID NO: 48) | VQGTHXPFT (SEQ ID NO: 49) |
| 1G11 | Murine AβpE3-11 | GLTLSDAWMN (SEQ ID NO: 32) | EIRSKAYKHATYYAESVKG (SEQ ID NO: 33) | HGS (SEQ ID NO: 34) |
| 2E4 | Murine AβpE3-11 | GITLNDAWMT (SEQ ID NO: 38) | EIRNKANNHATNYAESVKG (SEQ ID NO: 39) | HSY (SEQ ID NO: 40) |
| Difference | | GXTLXDAWMX (SEQ ID NO: 50) | EIRXKAXXHATXYAESVKG (SEQ ID NO: 51) | HXX (SEQ ID NO: 52) |
| 1G11 | Murine AβpE3-11 | RASQGISSKMG (SEQ ID NO: 35) | HGTKLED (SEQ ID NO: 36) | VQYAQFPYT (SEQ ID NO: 37) |
| 2E4 | Murine AβpE3-11 | HASQGIRNNIG (SEQ ID NO: 41) | HGTKLED (SEQ ID NO: 42) | VQYDQFPYT (SEQ ID NO: 43) |
| Difference | | XASQGIXXXXG (SEQ ID NO: 53) | HGTKLED (SEQ ID NO: 36) | VQYXQFPYT (SEQ ID NO: 55) |

These conserved amino acids which are to be found between the antibodies generated against AβpE3 must account for particular amino acids that are important for recognising the AβpE3.

The invention thus relates to an antibody, in particular an isolated antibody, or a fragment thereof, specific for human AβpE3 which antibody comprises, or consists, of:
- a heavy chain variable region ($V_H$) CDR1 comprising GYTFTDYYX$_1$N (SEQ ID NO:56),
- a heavy chain variable region ($V_H$) CDR2 comprising WX$_2$X$_3$PGSGNX$_4$KYNEKFKG (SEQ ID NO:57),
- a heavy chain variable region ($V_H$) CDR3 comprising EGX$_5$X$_6$X$_7$Y (SEQ ID NO:58),
- a light chain variable region ($V_L$) CDR1 comprising KSSQSLLX$_8$SNGX$_9$X$_{10}$YLN (SEQ ID NO:59),
- a light chain variable region ($V_L$) CDR2 comprising X$_{11}$VSKLDS (SEQ ID NO:60), and
- a light chain variable region ($V_L$) CDR3 comprising VQGTHX$_{12}$PFT (SEQ ID NO:61);

wherein $X_1$ to $X_{12}$ symbolizes a natural amino acid.

In a further embodiment $X_1$ to $X_{12}$ may be selected as follows
$X_1$ is I or L,
$X_2$ is I or L, $X_3$ is Y or N and/or $X_4$ is V or T,
$X_5$ is I or L, $X_6$ is I or P and/or $X_7$ is V or D,
$X_8$ is H or Y, $X_9$ is E or K and/or $X_{10}$ is T or S,
$X_{11}$ is A or V, and/or
$X_{12}$ is Y or F.

The invention thus also relates to an antibody, in particular an isolated antibody, or a fragment thereof, specific for murine AβpE3 which antibody comprises, or consists, of:
- a heavy chain variable region ($V_H$) CDR1 comprising $GX_1TLX_2DAWMX_3$ (SEQ ID NO:62),
- a heavy chain variable region ($V_H$) CDR2 comprising $EIRX_4KAX_5X_6HATX_7YAESVKG$ (SEQ ID NO:63),
- a heavy chain variable region ($V_H$) CDR3 comprising $HX_8X_9$ (SEQ ID NO:64),
- a light chain variable region ($V_L$) CDR1 comprising $X_{10}ASQGIX_{11}X_{12}X_{13}X_{14}G$ (SEQ ID NO:65),
- a light chain variable region ($V_L$) CDR2 comprising HGTKLED (SEQ ID NO:36), and
- a light chain variable region ($V_L$) CDR3 comprising $VQYX_{15}QFPYT$ (SEQ ID NO:66)

wherein $X_1$ to $X_{15}$ symbolizes a natural amino acid.

In a further embodiment $X_1$ to $X_{15}$ may be selected as follows
$X_1$ is I or L, $X_2$ is S or N, and/or $X_3$ is N or T,
$X_4$ is S or N, $X_5$ is Y or N, $X_6$ is K or N, and/or $X_7$ is Y or N,
$X_8$ is G or S and or S $X_9$ is S or Y,
$X_{10}$ is R or H, $X_{11}$ is S or R, $X_{12}$ is S or N, $X_{13}$ is K or N, and/or $X_{14}$ is M or I, and/or
$X_{15}$ is A or D.

The antibody may be isolated and preferably be specific for human AβpE3 with a binding affinity ($K_D$) of about 100 nM to about 50 nM, or about 50 nM to about 10 nM, or about 10 nM to about 5 nM for the human pyroglutamated Aβ fragment pEFRHDSGYE (SEQ ID NO:67) or the murine fragment pEFGHDSGFE (SEQ ID NO:68).

The invention further relates to an in vitro method for making an antibody, or a fragment thereof, specific for human pyroglutamated Aβ fragment pEFRHDSGYE (SEQ ID NO:67) or the murine fragment pEFGHDSGFE (SEQ ID NO:68), which method comprises the step varying one or more of the amino acids X. X may be selected as outlined above. Any suitable method for constructing these fragments can be used, such as PCR, and sequencing followed by a screening and selection for antibodies with the above mentioned desired properties with regards to $K_D$ and affinity for AβpE3-11 as shown in the examples.

The present invention provides the antibodies of the invention produced by a host cell. In one embodiment, the invention provides a monoclonal antibody produced by clone 5C9 or 2E8. In another embodiment, the invention provides a monoclonal antibody produced by clone 2E4 or 1G11. In other embodiments, the invention provides an isolated antibody, or fragment thereof, that competes with binding with the monoclonal antibody produced by clone 5C9, 2E8, 2E4 or 1G11. Furthermore, the invention provides hybridoma cell line 5C9, 2E8, 2E4 or 1G11, or progeny thereof.

Accordingly the invention relates to an antibody, or a fragment thereof, comprising of:
- a heavy chain variable region ($V_H$) CDR1 comprising SEQ ID NO:12;
- a heavy chain variable region ($V_H$) CDR2 comprising SEQ ID NO:13;
- a heavy chain variable region ($V_H$) CDR3 comprising SEQ ID NO:14;
- a light chain variable region ($V_L$) CDR1 comprising SEQ ID NO:15;
- a light chain variable region ($V_L$) CDR2 comprising SEQ ID NO:16; and
- a light chain variable region ($V_L$) CDR3 comprising SEQ ID NO:17.

The antibody, or fragment thereof, may also comprise or consist of a heavy chain variable region ($V_H$) encoded by the nucleotide sequence of SEQ NO:4 or having the amino acid sequence of SEQ ID NO:5. The antibody, or fragment thereof, may further comprise or consist of a light chain variable region ($V_L$) encoded by the nucleotide sequence of SEQ NO:6 or having the amino acid sequence of SEQ ID NO:7. Alternatively, the antibody, or fragment thereof, may comprise or consist of the heavy chain variable region ($V_H$) and the light chain variable region ($V_L$).

In another embodiment the antibody, or a fragment thereof, comprises or consist of:
- a heavy chain variable region ($V_H$) CDR1 comprising SEQ ID NO:18;
- a heavy chain variable region ($V_H$) CDR2 comprising SEQ ID NO:19;
- a heavy chain variable region ($V_H$) CDR3 comprising SEQ ID NO:20;
- a light chain variable region ($V_L$) CDR1 comprising SEQ ID NO:21;
- a light chain variable region ($V_L$) CDR2 comprising SEQ ID NO:22; and
- a light chain variable region ($V_L$) CDR3 comprising SEQ ID NO:23.

The antibody, or fragment thereof, may comprise or consist of a heavy chain variable region ($V_H$) encoded by the nucleotide sequence of SEQ NO:8 or having the amino acid sequence of SEQ ID NO:9. The antibody, or fragment thereof, may further comprise or consist of a light chain variable region ($V_L$) encoded by the nucleotide sequence of SEQ NO:10 or having the amino acid sequence of SEQ ID NO:11. Alternatively, the antibody, or fragment thereof, may comprise or consist of the heavy chain variable region ($V_H$) and the light chain variable region ($V_L$).

In a further embodiment the antibody, or a fragment thereof, may comprise or consist of:
- a heavy chain variable region ($V_H$) CDR1 comprising SEQ ID NO:32;
- a heavy chain variable region ($V_H$) CDR2 comprising SEQ ID NO:33;
- a heavy chain variable region ($V_H$) CDR3 comprising SEQ ID NO:34;
- a light chain variable region ($V_L$) CDR1 comprising SEQ ID NO:35;
- a light chain variable region ($V_L$) CDR2 comprising SEQ ID NO:36; and
- a light chain variable region ($V_L$) CDR3 comprising SEQ ID NO:37.

The antibody, or fragment thereof, may comprise or consist of a heavy chain variable region ($V_H$) encoded by the nucleotide sequence of SEQ NO:24 or having the amino acid sequence of SEQ ID NO:25. The antibody, or fragment thereof, may further comprise or consist of a light chain variable region ($V_L$) encoded by the nucleotide sequence of SEQ NO:26 or having the amino acid sequence of SEQ ID NO:27. Alternatively, the antibody, or fragment thereof, may comprise or consist of the heavy chain variable region (V$_H$) and the light chain variable region (V$_L$).

In a still further embodiment the invention relates to an antibody, or a fragment thereof, comprising or consisting of:
- a heavy chain variable region (V$_H$) CDR1 comprising SEQ ID NO:38;
- a heavy chain variable region (V$_H$) CDR2 comprising SEQ ID NO:39;
- a heavy chain variable region (V$_H$) CDR3 comprising SEQ ID NO:40;
- a light chain variable region (V$_L$) CDR1 comprising SEQ ID NO:41;
- a light chain variable region (V$_L$) CDR2 comprising SEQ ID NO:42; and
- a light chain variable region (V$_L$) CDR3 comprising SEQ ID NO:43.

The antibody, or fragment thereof, may comprise or consist of a heavy chain variable region (V$_H$) encoded by the nucleotide sequence of SEQ NO:28 or having the amino acid sequence of SEQ ID NO:29. The antibody, or fragment thereof, may further comprise or consist of a light chain variable region (V$_L$) encoded by the nucleotide sequence of SEQ NO:30 or having the amino acid sequence of SEQ ID NO:31. Alternatively, the antibody, or fragment thereof, may comprise or consist of the heavy chain variable region (V$_H$) and the light chain variable region (V$_L$).

The antibodies mentioned above may, according to one embodiment, further have no more than 4 amino acid differences, or no more than 3 amino acid differences, or no more than 2 amino acid differences, or no more than 1 amino acid difference from said CDR1-3 (V$_H$ and/or V$_L$) sequences.

It is envisaged that the antibody, or fragment thereof, may be humanized, chimeric, or single-chain antibody.

Further the antibodies may be in a composition together with a pharmaceutically acceptable carrier, e.g. for use in the treatment of Alzheimer disease.

The invention also relates to a method of treating Alzheimer's Disease in a patient, comprising administering to the patient in need of such treatment, a therapeutically effective amount of an antibody of the invention or a composition as mentioned above The antibodies may further be used in a diagnostic method or as a diagnostic imagining ligand.

The fragments, or immunogenic fragments, consisting of the AβpE3-11 (pEFRHDSGYE) (SEQ ID NO:67) fragment and/or AβpE3-11-C (pE-FRHDSGYEC) (SEQ ID NO:2) fragment may be used for generating antibodies having a binding affinity (K$_D$) to such fragment of with a binding affinity (K$_D$) of about 100 nM to about 50 nM, or about 50 nM to about 10 nM, or about 10 nM to about 5 nM.

The invention further relates to a therapeutic composition consisting or comprising of an AβpE3-11 (pEFRHDSGYE) (SEQ ID NO:67) fragment and/or the AβpE3-11-C (pE-FRHDSGYEC) (SEQ ID NO:2) fragment in an amount sufficient to elicit the production of antibodies, or an antibody that specifically binds to such fragment, and a pharmaceutically acceptable adjuvant or carrier.

The therapeutic composition may comprise one or more antibodies that binds to AβpE3-11 (pEFRHDSGYE) (SEQ ID NO:67) fragment and/or AβpE3-11-C (pE-FRHDSGYEC) (SEQ ID NO:2) fragment with a binding affinity (K$_D$) to such fragment of about with a binding affinity (K$_D$) of about 100 nM to about 50 nM, or about 50 nM to about 10 nM, or about 10 nM to about 5 nM.

The present invention provides the peptide AβpE3-11-C (pEFRHDSGYEC) (SEQ ID NO:2). In one embodiment, the present invention provides the peptide AβpE3-11-C dimer (pEFRHDSGYEC-CEYGSDHRFEp) (composed of two copies of SEQ ID NO:2 linked C-terminus to C-terminus). In another embodiment, the present invention provides polypeptide AβpE3-11-C-keyhole limpet hemocyanin: pEFRHDSGYEC-[KLH] (SEQ ID NO:2). The peptide AβpE3-11-C (pEFRHDSGYEC) (SEQ ID NO:2) conjugated to a carboxy-terminal carrier.

The present invention provides a method of immunizing an animal comprising administering AβpE3-11-C (pEFRHDSGYEC) (SEQ ID NO:2) as an immunogen.

The present invention provides a therapeutic composition comprising the AβpE3-11 (pEFRHDSGYE) (SEQ ID NO:67) and/or the AβpE3-11-C (pEFRHDSGYEC) (SEQ ID NO:2) fragment in an amount sufficient to elicit the production of antibodies, or an antibody that immunospecifically binds to such fragment.

The invention also relates to an in vitro method for making an antibody of, or a fragment thereof, specific for human pyroglutamated Aβ fragment pEFRHDSGYE (SEQ ID NO:67) and/or pE-FRHDSGYEC (SEQ ID NO:2) or specific for murine pyroglutamated Aβ fragment pEFGHDSGFE (SEQ ID NO:68) and/or pEFGHDSGFEC (SEQ ID NO:3), which method comprises the step varying one or more of the amino acids "X" given above. In particular the in vitro method the in vitro method may be suitable for making antibodies which binds with an affinity (KD) to said fragment of about 100 nM to about 50 nM, or about 50 nM to about 10 nM, or about 10 nM to about 5 nM The present invention relates to improvements in therapy and prevention of Alzheimer's disease (AD) and other diseases characterized by deposition of amyloid, e. g. characterized by amyloid deposits in the central nervous system (CNS).

The present invention also provides a method of reducing Aβ plaque formation in a patient, comprising administering to the patient in need of such treatment, a therapeutically effective amount of an antibody of the invention. In one embodiment, the Aβ plaques comprise pyroglutamated Aβ.

In one embodiment, the present invention provides a composition comprising the antibody described herein and a pharmaceutically acceptable carrier. In some embodiments, the composition of the invention is provided for use in the treatment of Alzheimer disease, or in the treatment of a neurodegenerative or cognitive disease or disorder.

The present invention also provides a method of treating Alzheimer's Disease in a patient, comprising administering to the patient in need of such treatment, a therapeutically effective amount of an antibody of the invention. The present invention also provides a method of treating neurodegenerative or cognitive disease or disorder in a patient, comprising administering to the patient in need of such treatment, a therapeutically effective amount of an antibody of the invention.

There are important parallels between AD and other neurological diseases, including prion diseases (such as kuru, Creutzfeld-Jacob disease and bovine spongiform encephalitis), Parkinson's disease, Huntington's disease, and fronto-temporal dementia. All involve deposits of abnormal proteins in the brain. AD and prion diseases cause dementia and death, and both are associated with the formation of insoluble amyloid fibrils, but from membrane proteins that are different from each other.

Monoclonal antibodies of the present invention may e.g. be produced by the hybridoma method first described by Kohler et al., Nature 256, 495 (1975), or may be produced by recombinant DNA methods. Monoclonal antibodies may also be isolated from phage antibody libraries using the techniques described in, for example, Clackson et al., *Nature* 352, 624-628 (1991) and Marks et al., *J. Mol. Biol.* 222, 581-597 (1991). Monoclonal antibodies may be obtained from any suitable source. Thus, for example, monoclonal antibodies may be obtained from hybridomas prepared from murine splenic B lymphocyte cells obtained from mice immunized with an antigen of interest, for instance, in the form of cells expressing the antigen on the surface, or a nucleic acid encoding an antigen of interest. Monoclonal antibodies may also be obtained from hybridomas derived from antibody-expressing cells of immunized humans or non-human mammals such as rats, rabbits, dogs, primates, etc.

In one embodiment, the antibody of the invention is a human antibody. Human monoclonal antibodies directed against Aβ may be generated using transgenic or transchromosomal mice carrying parts of the human immune system rather than the mouse system. Such transgenic and transchromosomic mice include mice referred to herein as HuMAb mice and KM mice, respectively, and are collectively referred to herein as "transgenic mice".

The HuMAb mouse contains a human immunoglobulin gene miniloci that encodes unrearranged human heavy variable and constant (μ and Y) and light variable and constant (K) chain immunoglobulin sequences, together with targeted mutations that inactivate the endogenous p and K chain loci (Lonberg, N. et al., *Nature* 368, 856-859 (1994)). Accordingly, the mice exhibit reduced expression of mouse IgM or K and in response to immunization, the introduced human heavy and light chain transgenes, undergo class switching and somatic mutation to generate high affinity human IgG, κ monoclonal antibodies (Lonberg, N. et al. (1994), supra; reviewed in Lonberg, N., Handbook of Experimental Pharmacology 113, 49-101 (1994), Lonberg, N. and Huszar, D., *Intern. Rev. Immunol.* Vol. 13 65-93 (1995) and Harding, F. and Lonberg, N., *Ann. N. Y. Acad. Sci* 764 536-546 (1995)). The preparation of HuMAb mice is described in detail in Taylor, L. et al., *Nucleic Acids Research* 20, 6287-6295 (1992), Chen, J. et al., *International Immunology* 5, 647-656 (1993), Tuaillon et al., *J. Immunol.* 152, 2912-2920 (1994), Taylor, L. et al., *International Immunology* 6, 579-591 (1994), Fishwild, D. et al., *Nature Biotechnology* 14, 845-851 (1996). See also U.S. Pat. Nos. 5,545,806, 5,569,825, 5,625,126, 5,633,425, 5,789,650, 5,877,397, 5,661,016, 5,814,318, 5,874,299, 5,770,429, 5,545,807, WO 98/24884, WO 94/25585, WO 93/1227, WO 92/22645, WO 92/03918 and WO 01/09187.

The HCo7 mice have a JKD disruption in their endogenous light chain (kappa) genes (as described in Chen et al., *EMBO J.* 12, 821-830 (1993)), a CMD disruption in their endogenous heavy chain genes (as described in Example 1 of WO 01/14424), a KCo5 human kappa light chain transgene (as described in Fishwild et al., *Nature Biotechnology* 14, 845-851 (1996)), and a HCo7 human heavy chain transgene (as described in U.S. Pat. No. 5,770,429).

The HCo12 mice have a JKD disruption in their endogenous light chain (kappa) genes (as described in Chen et al., *EMBO J.* 12, 821-830 (1993)), a CMD disruption in their endogenous heavy chain genes (as described in Example 1 of WO 01/14424), a KCo5 human kappa light chain transgene (as described in Fishwild et al., *Nature Biotechnology* 14, 845-851 (1996)), and a HCo12 human heavy chain transgene (as described in Example 2 of WO 01/14424).

In the KM mouse strain, the endogenous mouse kappa light chain gene has been homozygously disrupted as described in Chen et al., *EMBO J.* 12, 811-820 (1993) and the endogenous mouse heavy chain gene has been homozygously disrupted as described in Example 1 of WO 01/09187. This mouse strain carries a human kappa light chain transgene, KCo5, as described in Fishwild et al., *Nature Biotechnology* 14, 845-851 (1996). This mouse strain also carries a human heavy chain transchromosome composed of chromosome 14 fragment hCF (5C20) as described in WO 02/43478.

Splenocytes from these transgenic mice may be used to generate hybridomas that secrete human monoclonal antibodies according to well known techniques. Human monoclonal or polyclonal antibodies of the present invention, or antibodies of the present invention originating from other species may also be generated transgenically through the generation of another non-human mammal or plant that is transgenic for the immunoglobulin heavy and light chain sequences of interest and production of the antibody in a recoverable form therefrom. In connection with the transgenic production in mammals, antibodies may be produced in, and recovered from, the milk of goats, cows, or other mammals. See for instance U.S. Pat. Nos. 5,827,690, 5,756, 687, 5,750,172 and 5,741,957.

Further, human antibodies of the present invention or antibodies of the present invention from other species may be generated through display-type technologies, including, without limitation, phage display, retroviral display, ribosomal display, and other techniques, using techniques well known in the art and the resulting molecules may be subjected to additional maturation, such as affinity maturation, as such techniques are well known in the art (see for instance Hoogenboom et al., *J. Mol. Biol.* 227, 381 (1991) (phage display), Vaughan et al., *Nature Biotech* 14, 309 (1996) (phage display), Hanes and Plucthau, *PNAS USA* 94, 4937-4942 (1997) (ribosomal display), Parmley and Smith, *Gene* 73, 305-318 (1988) (phage display), Scott *TIBS* 17, 241-245 (1992), Cwirla et al., *PNAS USA* 87, 6378-6382 (1990), Russel et al., *Nucl. Acids Research* 21, 1081-1085 (1993), Hogenboom et al., *Immunol. Reviews* 130, 43-68 (1992), Chiswell and McCafferty *TIBTECH* 10, 80-84 (1992), and U.S. Pat. No. 5,733,743). If display technologies are utilized to produce antibodies that are not human, such antibodies may be humanized.

The antibody of the invention may be of any isotype. The choice of isotype typically will be guided by the desired effector functions, such as ADCC induction. Exemplary isotypes are IgG1, IgG2, IgG3, and IgG4. Either of the human light chain constant regions, kappa or lambda, may be used. If desired, the class of an anti-AβpE3 antibody of the present invention may be switched by known methods. For example, an antibody of the present invention that was originally IgM may be class switched to an IgG antibody of the present invention. Further, class switching techniques may be used to convert one IgG subclass to another, for instance from IgG1 to IgG2. Thus, the effector function of the antibodies of the present invention may be changed by isotype switching to, e.g., an IgG1, IgG2, IgG3, IgG4, IgD, IgA, IgE, or IgM antibody for various therapeutic uses. In one embodiment an antibody of the present invention is an IgG1 antibody, for instance an IgG1, κ.

In one embodiment, the antibody of the invention is a full-length antibody, preferably an IgG antibody, in particular an IgG1, κ antibody. In another embodiment, the antibody of the invention is an antibody fragment or a single-chain antibody.

Antibodies fragments may e.g. be obtained by fragmentation using conventional techniques, and the fragments screened for utility in the same manner as described herein for whole antibodies. For example, F(ab')$_2$ fragments may be generated by treating antibody with pepsin. The resulting F(ab')$_2$ fragment may be treated to reduce disulfide bridges to produce Fab' fragments. Fab fragments may be obtained by treating an IgG antibody with papain; Fab' fragments may be obtained with pepsin digestion of IgG antibody. An F(ab') fragment may also be produced by binding Fab' described below via a thioether bond or a disulfide bond. A Fab' fragment is an antibody fragment obtained by cutting a disulfide bond of the hinge region of the F(ab')$_2$. A Fab' fragment may be obtained by treating an F(ab')$_2$ fragment with a reducing agent, such as dithiothreitol. Antibody fragment may also be generated by expression of nucleic acids encoding such fragments in recombinant cells (see for instance Evans et al., *J. Immunol. Meth.* 184, 123-38 (1995)). For example, a chimeric gene encoding a portion of an F(ab')$_2$ fragment could include DNA sequences encoding the C$_H$1 domain and hinge region of the H chain, followed by a translational stop codon to yield such a truncated antibody fragment molecule.

In one embodiment, anti-AβpE3 antibody is a monovalent antibody, preferably a monovalent antibody as described in WO2007059782 (which is incorporated herein by reference in its entirety) having a deletion of the hinge region. Accordingly, in one embodiment, the antibody is a monovalent antibody, wherein said anti-pE3Aβ antibody is constructed by a method comprising:

(i) providing a nucleic acid construct encoding the light chain of said monovalent antibody, said construct comprising a nucleotide sequence encoding the V$_L$ region of a selected antigen specific anti-AβpE3 antibody and a nucleotide sequence encoding the constant C$_L$ region of an Ig, wherein said nucleotide sequence encoding the V$_L$ region of a selected antigen specific antibody and said nucleotide sequence encoding the C$_L$ region of an Ig are operably linked together, and wherein, in case of an IgG1 subtype, the nucleotide sequence encoding the C$_L$ region has been modified such that the C$_L$ region does not contain any amino acids capable of forming disulfide bonds or covalent bonds with other peptides comprising an identical amino acid sequence of the C$_L$ region in the presence of polyclonal human IgG or when administered to an animal or human being;

(ii) providing a nucleic acid construct encoding the heavy chain of said monovalent antibody, said construct comprising a nucleotide sequence encoding the V$_H$ region of a selected antigen specific antibody and a nucleotide sequence encoding a constant C$_H$ region of a human Ig, wherein the nucleotide sequence encoding the C$_H$ region has been modified such that the region corresponding to the hinge region and, as required by the Ig subtype, other regions of the C$_H$ region, such as the C$_H$3 region, does not comprise any amino acid residues which participate in the formation of disulphide bonds or covalent or stable non-covalent inter-heavy chain bonds with other peptides comprising an identical amino acid sequence of the C$_H$ region of the human Ig in the presence of polyclonal human IgG or when administered to an animal human being, wherein said nucleotide sequence encoding the V$_H$ region of a selected antigen specific antibody and said nucleotide sequence encoding the C$_H$ region of said Ig are operably linked together;

(iii) providing a cell expression system for producing said monovalent antibody; and (iv) producing said monovalent antibody by co-expressing the nucleic acid constructs of (i) and (ii) in cells of the cell expression system of (iii).

Similarly, in one embodiment, the anti-AβpE3 antibody is a monovalent antibody, which comprises:

(i) a variable region of an antibody of the invention as described herein or an antigen binding part of the said region, and (ii) a C$_H$ region of an immunoglobulin or a fragment thereof comprising the C$_H$2 and C$_H$3 regions, wherein the C$_H$ region or fragment thereof has been modified such that the region corresponding to the hinge region and, if the immunoglobulin is not an IgG4 subtype, other regions of the C$_H$ region, such as the C$_H$3 region, do not comprise any amino acid residues, which are capable of forming disulfide bonds with an identical C$_H$ region or other covalent or stable non-covalent inter-heavy chain bonds with an identical C$_H$ region in the presence of polyclonal human IgG.

In a further embodiment, the heavy chain of the monovalent anti-AβpE3 antibody has been modified such that the entire hinge has been deleted.

In another further embodiment, the sequence of said monovalent antibody has been modified so that it does not comprise any acceptor sites for N-linked glycosylation.

Anti-AβpE3 antibodies of the invention also include single chain antibodies. Single chain antibodies are peptides in which the heavy and light chain Fv regions are connected. In one embodiment, the present invention provides a single-chain Fv (scFv) wherein the heavy and light chains in the Fv of an anti-AβpE3 antibody of the present invention are joined with a flexible peptide linker (typically of about 10, 12, 15 or more amino acid residues) in a single peptide chain. Methods of producing such antibodies are described in for instance U.S. Pat. No. 4,946,778, Pluckthun in The Pharmacology of Monoclonal Antibodies, vol. 113, Rosenburg and Moore eds. Springer-Verlag, New York, pp. 269-315 (1994), Bird et al., *Science* 242, 423-426 (1988), Huston et al., *PNAS USA* 85, 5879-5883 (1988) and McCafferty et al., *Nature* 348, 552-554 (1990). The single chain antibody may be monovalent, if only a single V$_H$ and V$_L$ are used, bivalent, if two V$_H$ and V$_L$ are used, or polyvalent, if more than two V$_H$ and V$_L$ are used.

In general, anti-AβpE3 antibodies described herein may be modified by inclusion of any suitable number of such modified amino acids and/or associations with such conjugated substituents. Suitability in this context is generally determined by the ability to at least substantially retain AβpE3 selectivity and/or specificity associated with the non-derivatized parent anti-AβpE3 antibody. The inclusion of one or more modified amino acids may be advantageous in, for example, increasing polypeptide serum half-life, reducing polypeptide antigenicity, or increasing polypeptide storage stability. Amino acid(s) are modified, for example, co-translationally or post-translationally during recombinant production (e.g., N-linked glycosylation at N-X-S/T motifs during expression in mammalian cells) or modified by synthetic means. Non-limiting examples of a modified amino acid include a glycosylated amino acid, a sulfated amino acid, a prenylated (e. g., farnesylated, geranylgeranylated) amino acid, an acetylated amino acid, an acylated amino acid, a PEGylated amino acid, a biotinylated amino acid, a carboxylated amino acid, a phosphorylated amino acid, and the like. References adequate to guide one of skill in the modification of amino acids are replete throughout the literature. Example protocols are found in Walker (1998) Protein Protocols On CD-Rom, Humana Press, Totowa, N.J.

The modified amino acid may, for instance, be selected from a glycosylated amino acid, a PEGylated amino acid, a farnesylated amino acid, an acetylated amino acid, a biotinylated amino acid, an amino acid conjugated to a lipid moiety, or an amino acid conjugated to an organic derivatizing agent.

Anti-AβpE3 antibodies may also be chemically modified by covalent conjugation to a polymer to for instance increase their circulating half-life. Exemplary polymers, and methods to attach them to peptides, are illustrated in for instance U.S. Pat. Nos. 4,766,106, 4,179,337, 4,495,285 and 4,609,546. Additional illustrative polymers include polyoxyethylated polyols and polyethylene glycol (PEG) (e.g., a PEG with a molecular weight of between about 1,000 and about 40,000, such as between about 2,000 and about 20,000, e.g., about 3,000-12,000 g/mol).

In one embodiment, anti-AβpE3 antibodies comprising one or more radiolabeled amino acids are provided. A radiolabeled anti-AβpE3 antibody may be used for both diagnostic and therapeutic purposes (conjugation to radiolabeled molecules is another possible feature). Non-limiting examples of labels for polypeptides include, but are not limited to 3H, 14C, 15N, 35S, 90Y, 99Tc, and 125I, 131I, and 186Re. Methods for preparing radiolabeled amino acids and related peptide derivatives are known in the art (see for instance Junghans et al., in *Cancer Chemotherapy and Biotherapy* 655-686 (2nd edition, Chafner and Longo, eds., Lippincott Raven (1996)) and U.S. Pat. Nos. 4,681,581, 4,735,210, 5,101,827, 5,102,990 (U.S. RE35,500), U.S. Pat. Nos. 5,648,471 and 5,697,902. For example, a radioisotope may be conjugated by a chloramine T method.

In a further aspect, the invention relates to an expression vector encoding an antibody of the invention. Such expression vectors may be used for recombinant production of antibodies of the invention.

An expression vector in the context of the present invention may be any suitable vector, including chromosomal, non-chromosomal, and synthetic nucleic acid vectors (a nucleic acid sequence comprising a suitable set of expression control elements). Examples of such vectors include derivatives of SV40, bacterial plasmids, phage DNA, baculovirus, yeast plasmids, vectors derived from combinations of plasmids and phage DNA, and viral nucleic acid (RNA or DNA) vectors. In one embodiment, an anti-AβpE3 antibody-encoding nucleic acid is comprised in a naked DNA or RNA vector, including, for example, a linear expression element (as described in, for instance, Sykes and Johnston, *Nat Biotech* 12, 355-59 (1997)), a compacted nucleic acid vector (as described in for instance U.S. Pat. No. 6,077,835 and/or WO 00/70087), a plasmid vector such as pBR322, pUC 19/18, or pUC 118/119, a "midge" minimally-sized nucleic acid vector (as described in, for instance, Schakowski et al., *Mol Ther* 3, 793-800 (2001)), or as a precipitated nucleic acid vector construct, such as a CaPO₄-precipitated construct (as described in, for instance, WO 00/46147, Benvenisty and Reshef, *PNAS USA* 83, 9551-55 (1986), Wigler et al., *Cell* 14, 725 (1978), and Coraro and Pearson, *Somatic Cell Genetics* 2, 603 (1981)). Such nucleic acid vectors and the usage thereof are well known in the art (see for instance U.S. Pat. Nos. 5,589,466 and 5,973,972).

In one embodiment, the vector is suitable for expression of anti-AβpE3 antibody in a bacterial cell. Examples of such vectors include expression vectors such as BlueScript (Stratagene), pIN vectors (Van Heeke & Schuster, *J Biol Chem* 264, 5503-5509 (1989), pET vectors (Novagen, Madison, Wis.) and the like).

An expression vector may also or alternatively be a vector suitable for expression in a yeast system. Any vector suitable for expression in a yeast system may be employed. Suitable vectors include, for example, vectors comprising constitutive or inducible promoters such as alpha factor, alcohol oxidase and PGH (reviewed in: F. Ausubel et al., ed. Current Protocols in Molecular Biology, Greene Publishing and Wiley InterScience New York (1987), and Grant et al., *Methods in Enzymol* 153, 516-544 (1987)).

In an expression vector of the invention, anti-AβpE3 antibody-encoding nucleic acids may comprise or be associated with any suitable promoter, enhancer, and other expression-facilitating elements. Examples of such elements include strong expression promoters (e. g., human CMV IE promoter/enhancer as well as RSV, SV40, SL3-3, MMTV, and HIV LTR promoters), effective poly (A) termination sequences, an origin of replication for plasmid product in *E. coli*, an antibiotic resistance gene as selectable marker, and/or a convenient cloning site (e.g., a polylinker). Nucleic acids may also comprise an inducible promoter as opposed to a constitutive promoter such as CMV IE (the skilled artisan will recognize that such terms are actually descriptors of a degree of gene expression under certain conditions).

In an even further aspect, the invention relates to a recombinant eukaryotic or prokaryotic host cell, such as a transfectoma, which produces an antibody of the invention as defined herein or a bispecific molecule of the invention as defined herein. Examples of host cells include yeast, bacterial, and mammalian cells, such as CHO or HEK cells. For example, in one embodiment, the present invention provides a cell comprising a nucleic acid stably integrated into the cellular genome that comprises a sequence coding for expression of an anti-AβpE3 antibody of the present invention. In another embodiment, the present invention provides a cell comprising a non-integrated nucleic acid, such as a plasmid, cosmid, phagemid, or linear expression element, which comprises a sequence coding for expression of an anti-AβpE3 antibody of the invention.

In a further aspect, the invention relates to a method for producing an anti-AβpE3 antibody of the invention, said method comprising the steps of a) culturing a hybridoma or a host cell of the invention as described herein above, and b) purifying the antibody of the invention from the culture media.

In an even further aspect, the invention relates to a pharmaceutical composition comprising:
(i) an anti-AβpE3 antibody as defined herein or a bispecific molecule as defined herein, and
(ii) a pharmaceutically-acceptable carrier.

The pharmaceutical compositions may be formulated with pharmaceutically acceptable carriers or diluents as well as any other known adjuvants and excipients in accordance with conventional techniques such as those disclosed in Remington: The Science and Practice of Pharmacy, 21th Edition, Gennaro, Ed., Mack Publishing Co., Easton, Pa., 2005.

The pharmaceutically acceptable carriers or diluents as well as any other known adjuvants and excipients should be suitable for the chosen compound of the present invention and the chosen mode of administration. Suitability for carriers and other components of pharmaceutical compositions is determined based on the lack of significant negative impact on the desired biological properties of the chosen compound or pharmaceutical composition of the present invention (e.g., less than a substantial impact (10% or less relative inhibition, 5% or less relative inhibition, etc.)) on antigen binding.

A pharmaceutical composition of the present invention may also include diluents, fillers, salts, buffers, detergents (e.g., a nonionic detergent, such as Tween-20 or Tween-80), stabilizers (e.g., sugars or protein-free amino acids), preservatives, tissue fixatives, solubilizers, and/or other materials suitable for inclusion in a pharmaceutical composition.

The actual dosage levels of the active ingredients in the pharmaceutical compositions of the present invention may be varied so as to obtain an amount of the active ingredient which is effective to achieve the desired therapeutic response for a particular patient, composition, and mode of administration. The selected dosage level will depend upon a variety of pharmacokinetic factors including the activity of the particular compositions of the present invention employed, or the amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

The pharmaceutical composition may be administered by any suitable route and mode. Suitable routes of administering a compound of the present invention in vivo and in vitro are well known in the art and may be selected by those of ordinary skill in the art.

In one embodiment, a pharmaceutical composition of the present invention is administered parenterally.

The phrases "parenteral administration" and "administered parenterally" as used herein means modes of administration other than enteral and topical administration, usually by injection, and include epidermal, intravenous, intramuscular, intraarterial, intrathecal, intracapsular, intraorbital, intracardiac, intradermal, intraperitoneal, intratendinous, transtracheal, subcutaneous, subcuticular, intraarticular, subcapsular, subarachnoid, intraspinal, intracranial, intrathoracic, epidural and intrasternal injection and infusion.

In one embodiment that pharmaceutical composition is administered by intravenous or subcutaneous injection or infusion.

Pharmaceutically acceptable carriers include any and all suitable solvents, dispersion media, coatings, antibacterial and antifungal agents, isotonicity agents, antioxidants and absorption delaying agents, and the like that are physiologically compatible with a compound of the present invention.

Examples of suitable aqueous and nonaqueous carriers which may be employed in the pharmaceutical compositions of the present invention include water, saline, phosphate buffered saline, ethanol, dextrose, polyols (such as glycerol, propylene glycol, polyethylene glycol, and the like), and suitable mixtures thereof, vegetable oils, such as olive oil, corn oil, peanut oil, cottonseed oil, and sesame oil, carboxymethyl cellulose colloidal solutions, tragacanth gum and injectable organic esters, such as ethyl oleate, and/or various buffers. Other carriers are well known in the pharmaceutical arts.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the present invention is contemplated.

Proper fluidity may be maintained, for example, by the use of coating materials, such as lecithin, by the maintenance of the required particle size in the case of dispersions, and by the use of surfactants.

Pharmaceutical compositions of the present invention may also comprise pharmaceutically acceptable antioxidants for instance (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Pharmaceutical compositions of the present invention may also comprise isotonicity agents, such as sugars, polyalcohols, such as mannitol, sorbitol, glycerol or sodium chloride in the compositions.

The pharmaceutical compositions of the present invention may also contain one or more adjuvants appropriate for the chosen route of administration such as preservatives, wetting agents, emulsifying agents, dispersing agents, preservatives or buffers, which may enhance the shelf life or effectiveness of the pharmaceutical composition. The compounds of the present invention may be prepared with carriers that will protect the compound against rapid release, such as a controlled release formulation, including implants, transdermal patches, and microencapsulated delivery systems. Such carriers may include gelatin, glyceryl monostearate, glyceryl distearate, biodegradable, biocompatible polymers such as ethylene vinyl acetate, polyanhydrides, polyglycolic acid, collagen, polyorthoesters, and polylactic acid alone or with a wax, or other materials well known in the art. Methods for the preparation of such formulations are generally known to those skilled in the art. See, e.g., Sustained and Controlled Release Drug Delivery Systems, J. R. Robinson, ed., Marcel Dekker, Inc., New York, 1978.

In one embodiment, the compounds of the present invention may be formulated to ensure proper distribution in vivo. Pharmaceutically acceptable carriers for parenteral administration include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the present invention is contemplated. Supplementary active compounds may also be incorporated into the compositions.

Pharmaceutical compositions for injection must typically be sterile and stable under the conditions of manufacture and storage. The composition may be formulated as a solution, microemulsion, liposome, or other ordered structure suitable to high drug concentration. The carrier may be a aqueous or nonaqueous solvent or dispersion medium containing for instance water, ethanol, polyols (such as glycerol, propylene glycol, polyethylene glycol, and the like), and suitable mixtures thereof, vegetable oils, such as olive oil, and injectable organic esters, such as ethyl oleate. The proper fluidity may be maintained, for example, by the use of a coating such as lecithin, by the maintenance of the required particle size in the case of dispersion and by the use of surfactants. In many cases, it will be preferable to include isotonic agents, for example, sugars, polyalcohols such as glycerol, mannitol, sorbitol, or sodium chloride in the composition. Prolonged absorption of the injectable compositions may be brought about by including in the composition an agent that delays absorption, for example, monostearate salts and gelatin. Sterile injectable solutions may be prepared by incorporating the active compound in the required amount in an appropriate solvent with one or a combination of ingredients e.g. as enumerated above, as required, followed by sterilization microfiltration. Generally, dispersions are prepared by incorporating the active compound into a sterile vehicle that contains a basic dispersion medium and the required other ingredients e.g. from those enumerated above. In the case of sterile powders for the preparation of sterile injectable solutions, examples of methods of preparation are vacuum drying and freeze-drying (lyophilization) that yield a powder of the active ingredient plus any additional desired ingredient from a previously sterile-filtered solution thereof.

Sterile injectable solutions may be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, examples of methods of preparation are vacuum drying and freeze-drying (lyophilization) that yield a powder of the active ingredient plus any additional desired ingredient from a previously sterile-filtered solution thereof.

Dosage regimens in the above methods of treatment and uses are adjusted to provide the optimum desired response (e.g., a therapeutic response). For example, a single bolus may be administered, several divided doses may be administered over time or the dose may be proportionally reduced or increased as indicated by the exigencies of the therapeutic situation. Parenteral compositions may be formulated in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the present invention are dictated by and directly dependent on (a) the unique characteristics of the active compound and the particular therapeutic effect to be achieved, and (b) the limitations inherent in the art of compounding such an active compound for the treatment of sensitivity in individuals.

The effective dosages and the dosage regimens for the anti-AβpE3 antibodies depend on the disease or condition to be treated and may be determined by the persons skilled in the art. An exemplary, non-limiting range for a therapeutically effective amount of an antibody of the present invention is about 0.1-10 mg/kg/body weight, such as about 0.1-5 mg/kg/body weight, for example about 0.1-2 mg/kg/body weight, such as about 0.1-1 mg/kg/body weight, for instance about 0.15, about 0.2, about 0.5, about 1, about 1.5 or about 2 mg/kg/body weight.

A physician or veterinarian having ordinary skill in the art may readily determine and prescribe the effective amount of the pharmaceutical composition required. For example, the physician or veterinarian could start doses of the anti-AβpE3 antibody employed in the pharmaceutical composition at levels lower than that required in order to achieve the desired therapeutic effect and gradually increase the dosage until the desired effect is achieved. In general, a suitable daily dose of a composition of the present invention will be that amount of the compound which is the lowest dose effective to produce a therapeutic effect. Such an effective dose will generally depend upon the factors described above. Administration may e.g. be intravenous, intramuscular, intraperitoneal, or subcutaneous, and for instance administered proximal to the site of the target. If desired, the effective daily dose of a pharmaceutical composition may be administered as two, three, four, five, six or more sub-doses administered separately at appropriate intervals throughout the day, optionally, in unit dosage forms. While it is possible for a compound of the present invention to be administered alone, it is preferable to administer the compound as a pharmaceutical composition as described above.

Labeled antibodies of the invention can be used for diagnostic purposes to detect, diagnose, or monitor diseases or disorders. The invention provides for the detection or diagnosis of a neurodegenerative or cognitive disease or disorder, including but not limited to Alzheimer's Disease, comprising: (a) assaying the existence of pyroglutamated Aβ fragments in cells or tissue samples of a subject using one or more antibodies that immunospecifically bind to AβpE3; and (b) comparing the level of the antigen with a control level, e.g. levels in normal tissue samples, whereby an increase in the assayed level of antigen compared to the control level of antigen is indicative of the disease or disorder, or indicative of the severity of the disease or disorder.

Antibodies of the invention can be use to assay pyroglutamated Aβ fragments in a biological sample using immunohistochemical methods well-known in the art. Other antibody-based methods useful for detecting protein include immunoassays such as the enzyme linked immunoassay (ELISA) and the radioimmunoassay (RIA). Suitable antibody labels may be used in such kits and methods, and labels known in the art include enzyme labels, such as alkaline phosphatase and glucose oxidase; radioisotope labels, such as iodine ($^{125}$I, $^{131}$I), carbon ($^{14}$C), sulfur ($^{35}$S), tritium ($^{3}$H), indium ($^{121}$In), and technetium ($^{99m}$Tc); and luminescent labels, such as luminol and luciferase; and fluorescent labels, such as flourescein and rhodamine.

Presence of labeled antibodies may be detected in vivo for diagnosis purposes. In one embodiment, diagnosis comprises: a) administering to a subject an effective amount of a labeled antibody; b) waiting for a time interval following administration for permitting labeled antibody to concentrate at sites where Aβ may be detected and to allow for unbound labeled antibody to be cleared to background level; c) determining a background level; and d) detecting the labeled antibody in the subject, such that detection of labeled antibody above the background level is indicative that the subject has the disease or disorder, or is indicative of the severity of the disease or disorder. In accordance with such embodiment, the antibody is labeled with an imaging moiety suitable for detection using a particular imaging system known to those skilled in the art. Background levels may be determined by various methods known in the art, including comparing the amount of labeled antibody detected to a standard value previously determined for a particular imaging system. Methods and systems that may be used in the diagnostic methods of the invention include, but are not limited to, computed tomography (CT), whole body scan such as positron emission tomography (PET), magnetic resonance imaging (MRI), and sonography.

EXAMPLES

Example 1: Immunization and Screening

Pyroglutamated human Aβ3-11, with the addition of a C-terminal cysteine residue, pE-FRHDSGYE-C (SEQ ID NO:2) and pyroglutamated murine Aβ3-11, with the addition of a C-terminal cysteine residue, pE-FGHDSGFE-C (SEQ ID NO:3) was used in the immunisations. As such, mice were immunized with pE-FRHDSGYE-C or with pEFRHDSGYE-C each conjugated to KLH. The peptides were made and amplified using PCR and purified as disclosed in Sambrook (2000) Molecular Cloning, third edition, Cold Spring Harbor Laboratory Press The modified peptide was conjugated to a carrier protein, such as KLH. 10 Balb/c mice were immunized and boosted with a standard immunization protocol as outlined below

| Procedure | Scheduled days | Routes and dosages |
|---|---|---|
| 1st Immunization | 0 | 10-100 ug/0.25 ml animal, CFA |
| 2nd Immunization | 14 | 10-50 ug/0.25 ml animal, IFA |
| 3rd Immunization | 35 | 10-50 ug/0.25 ml animal, IFA |
| Final immunization | 56 | 10-50 ug/0.25 ml animal, Saline, |

Tail bleedings were screened by ELISA or other method if needed with pyroglutamate and non-pyroglutamate-peptide.

Fusion and Screening.

2 fusions (1-2 spleens per fusion) were performed on the best mice that responded the best to the pyroglutamate-peptide in Example 1.

The hybridoma cells were screened by ELISA or other method if needed with pyroglutamate and non-pyroglutamate-peptide and all positive clones were expanded into 24-well plates. The clones with best ELISA value and specificity to pyroglutamate-peptide were selected for subcloning.

Subcloning, Expansion, Cryopreservation and Delivery.

Hybridoma subclones were screened by ELISA with pyroglutamate and non-pyroglutamate-peptide. Up to five positive parental clones by limiting dilution, isotype the final positive supernatants, and expand and cryopreserve two subclones for each parental.

Antibodies were purified by protein A chromatography of media from cultured hybridoma cell.

Example 2: Characterization of Monoclonal Antibodies

Affinity measurements using SPR technology: Binding affinity of anti-Aβ antibodies was determined using BIAcore 3000 (Biacore, Upsula, Sweden). Human and murine pyroglutaminyl and unmodified Aβ peptides with a C-terminal Cystein were immobilized on a CM5 chip using the 2-(2-pyridinyldithio) ethaneamine hydrochloride (PDEA) coupling technology (GE healthcare).

Approximately 100 RU of peptide was immobilised. Antibody binding was determined at different concentrations and kinetic constant calculated from the combined set of data using bivalent binding kinetics. Association and dissociation constants were determined using BIAevaluation software (version 3.1).

The BIAcore binding is shown in FIG. 1A-1B.

Example 3: Immunohistochemistry Methods

Paraffin blocks of frontal cortex tissue from Alzheimer patients and from age-matched controls were obtained from Cambridge Bioscience (UK) and sectioned at 4 μm. Likewise, sections were prepared from brains of APP/PS1 double-transgenic mice carrying the APP Swedish mutation. Deparaffinised sections were subjected to antigen retrieval by microwave treatment in 10 mM Citrate buffer, pH 6, followed by 88% formic acid for 3 min. Sections were incubated o/n at 4° C. with primary antibodies: Anti-Abeta #6E10 at 1:100 (Covance, N.J., USA); pE3-Abeta antibodies (clone 2E8G6 and 5C9) at dilutions ranging from 3-20 μg/ml. This was followed by biotin-conjugated anti-mouse antibodies (#0464, DAKO, Denmark) at 1:500 and StreptAvidin-Biotin complex (Vector Laboratoreis, UK). The immunoreaction was developed in 0.05% diaminobenzidine+0.01% $H_2O_2$.

Binding studies indicated that the anti-AβpE3 antibodies, generated from the AβpE3-11 immunogen, are highly specific to pyroglutamated pE3 peptide. As such, the generated anti-AβpE3 antibodies bind with little or no affinity to the unmodified Aβ 3-11 peptide.

Further, antibodies raised against the human peptide did not bind the murine pyroglutamated peptide, and vice versa (see FIG. 1A-1B). Comparison of the human and the murine 3-11 amino acid sequences of Aβ reveals two amino acid residue differences at Aβ positions 4 and 10. We observe that the amino acid residue Y at position 10 in the human peptide may contribute to the higher degree of specificity seen by anti-human AβpE3 antibodies.

Figure 2B:
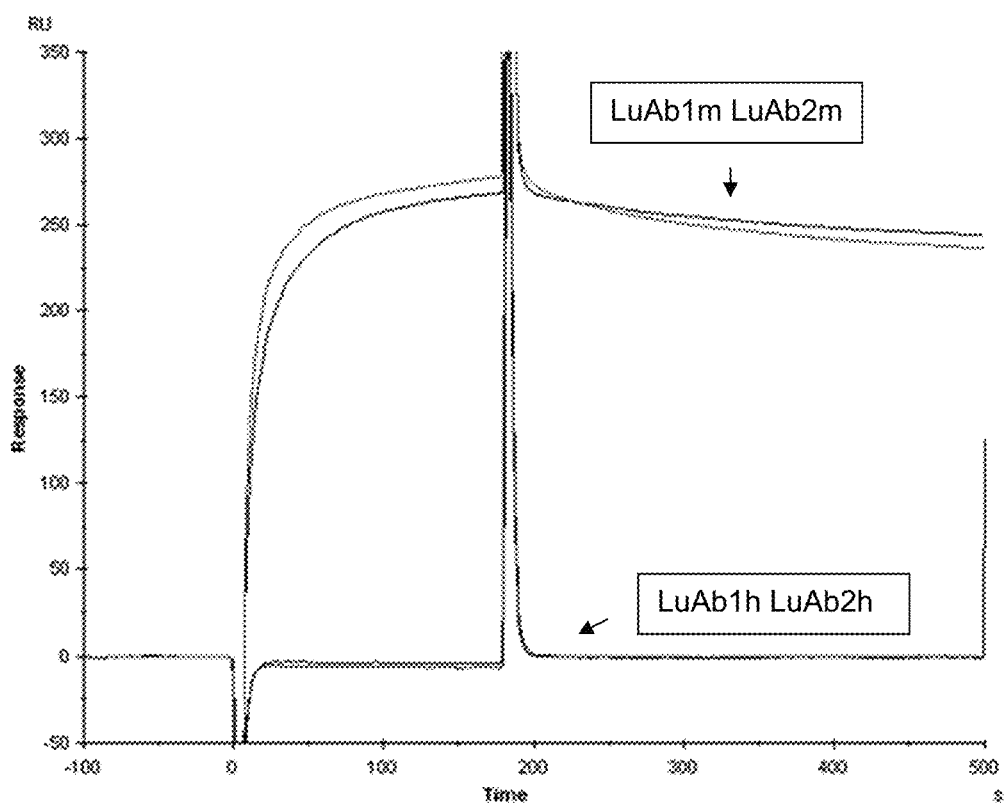
Figure 3A:
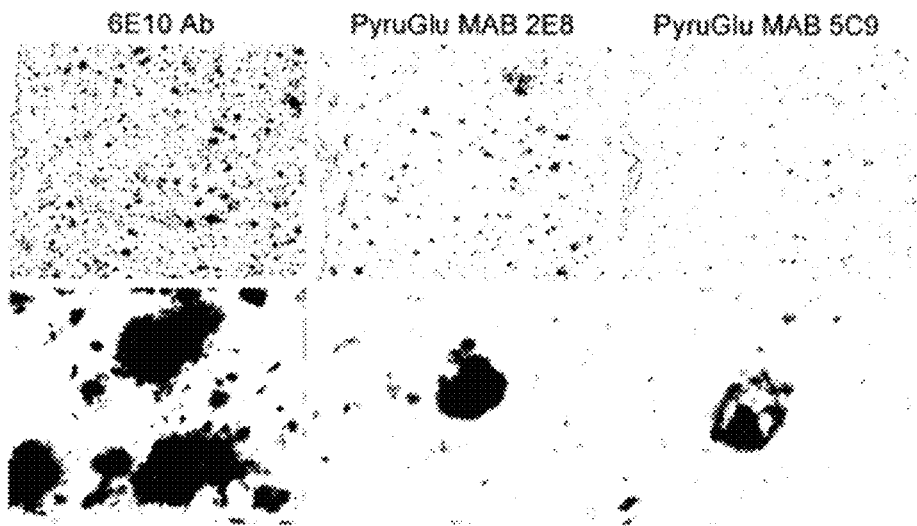
FIGS. 3A and 3B. Micrographs showing immunoreactivity of Abeta and pE3-Abeta antibodies in the frontal cortex from an Alzheimer brain (FIG. 3A) and in the hippocampal region of an APP/PS1 transgenic mouse (FIG. 3B). The antibodies used are 6E10, which is specific for Aβ, 2E8 and 5C9 which are specific for human AβpE.
Figure 3B:
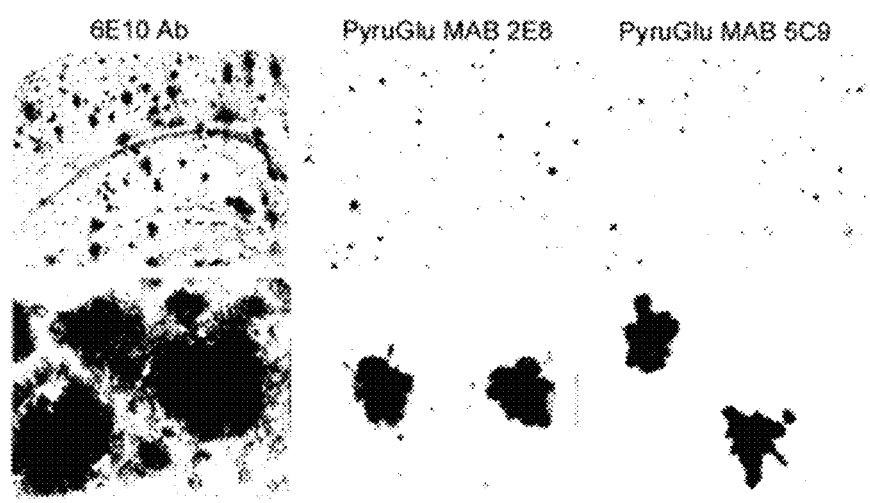

It was demonstrated by immunohistochemistry in brain samples from Alzheimer patients as well as APP/PS1 transgenic mice that the two anti-AβpE3 monoclonal antibodies 5C9 and 2E8 (which is another specific monoclonal antibody not claimed in this application) were able to bind to Abeta plaques (FIG. 2A-2B and FIG. 3A-3B). Immunostaining using a recognised commercial anti-Abeta antibody (clone 6E10) was compared to the anti-AβpE3 monoclonal antibodies 2E8 and 5C9. AβpE3 antibodies were shown to label only a subset of plaques at the dilutions tested, whereas intracellular Abeta and diffuse plaques were also stained by the 6E10 antibody. The intracellular Abeta and diffuse plaques were not detected by AβpE3 antibodies. All 3 antibodies clearly stained dense-core plaques. pE3-Abeta antibodies did not label structures in human cortex from non-demented controls.

Those skilled in the art will recognize that various changes and/or modifications may be made to aspects or embodiments of this invention and that such changes and/or modifications may be made without departing from the spirit of this invention. Therefore, it is intended that the appended claims cover all such equivalent variations as will fall within the spirit and scope of this invention.

Each reference cited in the present application, including literature references, books, patents and patent applications, is incorporated herein by reference in its entirety.

What is claimed is:

1. An IgG antibody, or a fragment thereof, wherein said antibody and said fragment are capable of specifically binding murine AβpE3 with a binding affinity ($K_D$) of about 100 nM to about 5 nm for the murine pyroglutamated Aβ fragment pEFGHDSGFE (SEQ ID NO:68), wherein said antibody comprises:
   (A) a heavy chain variable region ($V_H$) CDR1 comprising GLTLSDAWMN (SEQ ID NO:32) or GITLNDAWMT (SEQ ID NO:38);
   (B) a heavy chain variable region ($V_H$) CDR2 comprising EIRSKAYKHATYYAESVKG (SEQ ID NO:33) or EIRNKANNHATNYAESVKG (SEQ ID NO:39);
   (C) a heavy chain variable region ($V_H$) CDR3 comprising NO:64) HGS (SEQ ID NO:34) or HSY (SEQ ID NO:40);
   (D) a light chain variable region ($V_L$) CDR1 comprising RASQGISSKMG (SEQ ID NO:35) or HASQGIRNNIG (SEQ ID NO:41);
   (E) a light chain variable region ($V_L$) CDR2 comprising HGTKLED (SEQ ID NO:36) or HGTKLED (SEQ ID NO:42); and
   (F) a light chain variable region ($V_L$) CDR3 comprising VQYAQFPYT (SEQ ID NO:37) or VQYDQFPYT (SEQ ID NO:43).

2. The antibody, or said fragment thereof, of claim 1, wherein:
   (A) said heavy chain variable region ($V_H$) CDR1 comprises GLTLSDAWMN (SEQ ID NO:32);
   (B) said heavy chain variable region ($V_H$) CDR2 comprises EIRSKAYKHATYYAESVKG (SEQ ID NO:33);
   (C) said heavy chain variable region ($V_H$) CDR3 comprises HGS (SEQ ID NO:34);
   (D) said light chain variable region ($V_L$) CDR1 comprises RASQGISSKMG (SEQ ID NO:35);
   (E) said light chain variable region ($V_L$) CDR2 comprises HGTKLED (SEQ ID NO:36); and
   (F) said light chain variable region ($V_L$) CDR3 comprises VQYAQFPYT (SEQ ID NO:37).

3. The antibody, or said fragment thereof, of claim 2, wherein said antibody comprises:
   (A) a heavy chain variable region ($V_H$) that comprises the amino acid sequence of SEQ ID NO:25; and/or
   (B) a light chain variable region ($V_L$) that comprises the amino acid sequence of SEQ ID NO:27.

4. The antibody, or said fragment thereof, of claim 1, wherein:
   (A) said heavy chain variable region ($V_H$) CDR1 comprises GITLNDAWMT (SEQ ID NO:38);
   (B) said heavy chain variable region ($V_H$) CDR2 comprises EIRNKANNHATNYAESVKG (SEQ ID NO:39);

(C) said heavy chain variable region (V$_H$) CDR3 comprises HSY (SEQ ID NO:40);
(D) said light chain variable region (V$_L$) CDR1 comprises HASQGIRNNIG (SEQ ID NO:41);
(E) said light chain variable region (V$_L$) CDR2 comprises HGTKLED (SEQ ID NO:42); and
(F) said light chain variable region (V$_L$) CDR3 comprises VQYDQFPYT (SEQ ID NO:43).

5. The antibody, or said fragment thereof, of claim 4, wherein said antibody comprises:
(A) a heavy chain variable region (V$_H$) that comprises the amino acid sequence of SEQ ID NO:29; and/or
(B) a light chain variable region (V$_L$) that comprises the amino acid sequence of SEQ ID NO:31.

6. The antibody, or said fragment thereof, of claim 1, wherein said antibody is a humanized antibody, a chimeric antibody, or a single-chain antibody.

7. The antibody, or said fragment thereof, of claim 1, wherein said antibody or fragment is detectably labelled.

8. A pharmaceutical composition comprising the antibody, or said fragment thereof, of claim 1 and a pharmaceutically acceptable carrier.

9. The pharmaceutical composition of claim 8, wherein:
(A) said heavy chain variable region (V$_H$) CDR1 comprises GLTLSDAWMN (SEQ ID NO:32);
(B) said heavy chain variable region (V$_H$) CDR2 comprises EIRSKAYKHATYYAESVKG (SEQ ID NO:33);
(C) said heavy chain variable region (V$_H$) CDR3 comprises HGS (SEQ ID NO:34);
(D) said light chain variable region (V$_L$) CDR1 comprises RASQGISSKMG (SEQ ID NO:35);
(E) said light chain variable region (V$_L$) CDR2 comprises HGTKLED (SEQ ID NO:36); and
(F) said light chain variable region (V$_L$) CDR3 comprises VQYAQFPYT (SEQ ID NO:37).

10. The pharmaceutical composition of claim 9, wherein said antibody comprises:
(A) a heavy chain variable region (V$_H$) that comprises the amino acid sequence of SEQ ID NO:25; and/or
(B) a light chain variable region (V$_L$) that comprises the amino acid sequence of SEQ ID NO:27.

11. The pharmaceutical composition of claim 8, wherein:
(A) said heavy chain variable region (V$_H$) CDR1 comprises GITLNDAWMT (SEQ ID NO:38);
(B) said heavy chain variable region (V$_H$) CDR2 comprises EIRNKANNHATNYAESVKG (SEQ ID NO:39);
(C) said heavy chain variable region (V$_H$) CDR3 comprises HSY (SEQ ID NO:40);
(D) said light chain variable region (V$_L$) CDR1 comprises HASQGIRNNIG (SEQ ID NO:41);
(E) said light chain variable region (V$_L$) CDR2 comprises HGTKLED (SEQ ID NO:42); and
(F) said light chain variable region (V$_L$) CDR3 comprises VQYDQFPYT (SEQ ID NO:43).

12. The pharmaceutical composition of claim 11, wherein said antibody comprises:
(A) a heavy chain variable region (V$_H$) that comprises the amino acid sequence of SEQ ID NO:29; and/or
(B) a light chain variable region (V$_L$) that comprises the amino acid sequence of SEQ ID NO:31.

* * * * *

SEQUENCE LISTING

<160> NUMBER OF SEQ ID NOS: 68

<210> SEQ ID NO 1
<211> LENGTH: 42
<212> TYPE: PRT
<213> ORGANISM: Human

<400> SEQUENCE: 1

```
Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
                20                  25                  30

Gly Leu Met Val Gly Gly Val Val Ile Ala
            35                  40

<210> SEQ ID NO 2
<211> LENGTH: 10
<212> TYPE: PRT
<213> ORGANISM: Human
<220> FEATURE:
<221> NAME/KEY: Pyrrolidone carboxylic acid
<222> LOCATION: (1)..(1)
<223> OTHER INFORMATION: E in position 1 is pyrrolidone carboxylic acid

<400> SEQUENCE: 2

Glu Phe Arg His Asp Ser Gly Tyr Glu Cys
1               5                   10

<210> SEQ ID NO 3
<211> LENGTH: 10
<212> TYPE: PRT
<213> ORGANISM: murine
<220> FEATURE:
<221> NAME/KEY: Pyrrolidone carboxylic acid
<222> LOCATION: (1)..(1)
<223> OTHER INFORMATION: E in position 1 is pyrrolidone carboxylic acid

<400> SEQUENCE: 3

Glu Phe Gly His Asp Ser Gly Phe Glu Cys
1               5                   10

<210> SEQ ID NO 4
<211> LENGTH: 345
<212> TYPE: DNA
<213> ORGANISM: Artificial
<220> FEATURE:
<223> OTHER INFORMATION: antibody variable region

<400> SEQUENCE: 4
cagatccagc tgcagcagtc tggacctgag ctggtgaagc ctggggctgc agtgaagata      60
tcctgcaagg cttctggcta caccttcact gactactatt taaactgggt gaagcaaaag     120
cctggacagg gacttgagtg gattggatgg atttatcctg aagcggtaa tgttaaatat      180 aatgagaagt tcaagggcaa ggccacattg actgcagaca cttcctccaa cacagcccac     240
atgcagctca gcagcctgac atctgaggac actgctgtct atttctgtac aagagagggg     300
ctcattgttt attggggcca aggactctg gtcactgtct ctgca                       345

<210> SEQ ID NO 5
<211> LENGTH: 115
<212> TYPE: PRT
<213> ORGANISM: artificial
<220> FEATURE:
<223> OTHER INFORMATION: antibody variable region

<400> SEQUENCE: 5

Gln Ile Gln Leu Gln Gln Ser Gly Pro Glu Leu Val Lys Pro Gly Ala
1               5                   10                  15

Ala Val Lys Ile Ser Cys Lys Ala Ser Gly Tyr Thr Phe Thr Asp Tyr
                20                  25                  30

Tyr Leu Asn Trp Val Lys Gln Lys Pro Gly Gln Gly Leu Glu Trp Ile
            35                  40                  45
```

Gly Trp Ile Tyr Pro Gly Ser Gly Asn Val Lys Tyr Asn Glu Lys Phe
        50                  55                  60

Lys Gly Lys Ala Thr Leu Thr Ala Asp Thr Ser Asn Thr Ala His
65                  70                  75                  80

Met Gln Leu Ser Ser Leu Thr Ser Glu Asp Thr Ala Val Tyr Phe Cys
                85                  90                  95

Thr Arg Glu Gly Leu Ile Val Tyr Trp Gly Gln Gly Thr Leu Val Thr
                100                 105                 110

Val Ser Ala
        115

<210> SEQ ID NO 6
<211> LENGTH: 336
<212> TYPE: DNA
<213> ORGANISM: artificial
<220> FEATURE:
<223> OTHER INFORMATION: antibody variable region

<400> SEQUENCE: 6
gatgttgtgc tgacccagac tccattcact ttgtcggtta ccattggaca accagcctct    60
atctcttgca gtcaagtca gagcctctta catagtaatg gagaaagcta tttgaattgg   120
ttatttcaga ggccaggcca gtctccaaag cgcctaatct atgcggtgtc taaactggac   180
tctggagtcc ctgacaggtt cactggcagt ggatcaggaa cagattttac actgaaaatc   240
agcagagtgg aggctgagga tttgggagtt tattactgcg tgcaaggtac acattttccg   300
ttcacgttcg gagggggac caagctggaa ataaaa                             336

<210> SEQ ID NO 7
<211> LENGTH: 112
<212> TYPE: PRT
<213> ORGANISM: artificial
<220> FEATURE:
<223> OTHER INFORMATION: antibody variable region

<400> SEQUENCE: 7

Asp Val Val Leu Thr Gln Thr Pro Phe Thr Leu Ser Val Thr Ile Gly
1               5                   10                  15

Gln Pro Ala Ser Ile Ser Cys Lys Ser Gln Ser Leu Leu His Ser
            20                  25                  30

Asn Gly Glu Ser Tyr Leu Asn Trp Leu Phe Gln Arg Pro Gly Gln Ser
        35                  40                  45

Pro Lys Arg Leu Ile Tyr Ala Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Val Gln Gly
                85                  90                  95

Thr His Phe Pro Phe Thr Phe Gly Gly Gly Thr Lys Leu Glu Ile Lys
                100                 105                 110

<210> SEQ ID NO 8
<211> LENGTH: 345
<212> TYPE: DNA
<213> ORGANISM: artificial
<220> FEATURE:
<223> OTHER INFORMATION: antibody variable region

<400> SEQUENCE: 8
cagatccagc tgcagcagtc tggacctgac ctggtgaagc ctggggcttc agtgaagata 60
tcctgcaagg cttctggcta caccttcact gactactata taaactgggt caagcagaag 120
cctggacagg gacttgagtg gattggatgg cttaatcctg aagcggtaa tactaagtac 180 aatgagaagt tcaagggcaa ggccacaatg actgtggaca caacctccag tacagtttac 240
atgcagctca gcagcctgac atctgaggac tctgctgtct atttctgtac aagagaagga 300
cctatcgact actggggtcg aggaacctca gtcaccgtct cctca 345

```
<210> SEQ ID NO 9
<211> LENGTH: 115
<212> TYPE: PRT
<213> ORGANISM: artificial
<220> FEATURE:
<223> OTHER INFORMATION: antibody variable region

<400> SEQUENCE: 9
```

Gln Ile Gln Leu Gln Gln Ser Gly Pro Asp Leu Val Lys Pro Gly Ala
1               5                   10                  15

Ser Val Lys Ile Ser Cys Lys Ala Ser Gly Tyr Thr Phe Thr Asp Tyr
            20                  25                  30

Tyr Ile Asn Trp Val Lys Gln Lys Pro Gly Gln Gly Leu Glu Trp Ile
        35                  40                  45

Gly Trp Leu Asn Pro Gly Ser Gly Asn Thr Lys Tyr Asn Glu Lys Phe
    50                  55                  60

Lys Gly Lys Ala Thr Met Thr Val Asp Thr Ser Ser Thr Val Tyr
65                  70                  75                  80

Met Gln Leu Ser Ser Leu Thr Ser Glu Asp Ser Ala Val Tyr Phe Cys
                85                  90                  95

Thr Arg Glu Gly Pro Ile Asp Tyr Trp Gly Arg Gly Thr Ser Val Thr
            100                 105                 110

Val Ser Ser
        115

```
<210> SEQ ID NO 10
<211> LENGTH: 336
<212> TYPE: DNA
<213> ORGANISM: artificial
<220> FEATURE:
<223> OTHER INFORMATION: antibody variable region

<400> SEQUENCE: 10
```
gatgttgtgc tgacccagac tccactcact ttgtcggtta ccattggaca acccgcctct 60
atctcttgca gtcaagtca gagcctctta tatagtaatg gaaaaaccta tttgaattgg 120
ttattacaga ggccaggtca gtctccgaag cgcctaatct atgtggtgtc taaactggac 180
tctggagtcc ctgacaggtt cactggcagt ggatcaggaa cagatttcac actgaaaatc 240
agcagagtgg aggctgagga tttgggagtt tattactgcg tgcaaggtac acattatccg 300
ttcacgttcg gagggggac caagctggaa ataaaa 336

```
<210> SEQ ID NO 11
<211> LENGTH: 112
<212> TYPE: PRT
<213> ORGANISM: artificial
<220> FEATURE:
<223> OTHER INFORMATION: antibody variable region

<400> SEQUENCE: 11
```

Asp Val Val Leu Thr Gln Thr Pro Leu Thr Leu Ser Val Thr Ile Gly

```
            1               5                  10                 15
Gln Pro Ala Ser Ile Ser Cys Lys Ser Ser Gln Ser Leu Leu Tyr Ser
            20                 25                 30

Asn Gly Lys Thr Tyr Leu Asn Trp Leu Leu Gln Arg Pro Gly Gln Ser
            35                 40                 45

Pro Lys Arg Leu Ile Tyr Val Val Ser Lys Leu Asp Ser Gly Val Pro
            50                 55                 60

Asp Arg Phe Thr Gly Ser Gly Ser Gly Thr Asp Phe Thr Leu Lys Ile
65                  70                 75                 80

Ser Arg Val Glu Ala Glu Asp Leu Gly Val Tyr Tyr Cys Val Gln Gly
                    85                 90                 95

Thr His Tyr Pro Phe Thr Phe Gly Gly Gly Thr Lys Leu Glu Ile Lys
                    100                105                110

<210> SEQ ID NO 12
<211> LENGTH: 10
<212> TYPE: PRT
<213> ORGANISM: artificial
<220> FEATURE:
<223> OTHER INFORMATION: Complementarity determining region

<400> SEQUENCE: 12

Gly Tyr Thr Phe Thr Asp Tyr Tyr Leu Asn
1               5                  10

<210> SEQ ID NO 13
<211> LENGTH: 17
<212> TYPE: PRT
<213> ORGANISM: artificial
<220> FEATURE:
<223> OTHER INFORMATION: Complementarity determining region

<400> SEQUENCE: 13

Trp Ile Tyr Pro Gly Ser Gly Asn Val Lys Tyr Asn Glu Lys Phe Lys
1               5                  10                 15

Gly

<210> SEQ ID NO 14
<211> LENGTH: 6
<212> TYPE: PRT
<213> ORGANISM: artificial
<220> FEATURE:
<223> OTHER INFORMATION: Complementarity determining region

<400> SEQUENCE: 14

Glu Gly Leu Ile Val Tyr
1               5

<210> SEQ ID NO 15
<211> LENGTH: 16
<212> TYPE: PRT
<213> ORGANISM: artificial
<220> FEATURE:
<223> OTHER INFORMATION: Complementarity determining region

<400> SEQUENCE: 15

Lys Ser Ser Gln Ser Leu Leu His Ser Asn Gly Glu Ser Tyr Leu Asn
1               5                  10                 15

<210> SEQ ID NO 16
<211> LENGTH: 7
<212> TYPE: PRT
<213> ORGANISM: artificial
```

```
<220> FEATURE:
<223> OTHER INFORMATION: Complementarity determining region

<400> SEQUENCE: 16

Ala Val Ser Lys Leu Asp Ser
1               5

<210> SEQ ID NO 17
<211> LENGTH: 9
<212> TYPE: PRT
<213> ORGANISM: artificial
<220> FEATURE:
<223> OTHER INFORMATION: Complementarity determining region

<400> SEQUENCE: 17

Val Gln Gly Thr His Phe Pro Phe Thr
1               5

<210> SEQ ID NO 18
<211> LENGTH: 10
<212> TYPE: PRT
<213> ORGANISM: artificial
<220> FEATURE:
<223> OTHER INFORMATION: Complementarity determining region

<400> SEQUENCE: 18

Gly Tyr Thr Phe Thr Asp Tyr Tyr Ile Asn
1               5                   10

<210> SEQ ID NO 19
<211> LENGTH: 17
<212> TYPE: PRT
<213> ORGANISM: artificial
<220> FEATURE:
<223> OTHER INFORMATION: Complementarity determining region

<400> SEQUENCE: 19

Trp Leu Asn Pro Gly Ser Gly Asn Thr Lys Tyr Asn Glu Lys Phe Lys
1               5                   10                  15

Gly

<210> SEQ ID NO 20
<211> LENGTH: 6
<212> TYPE: PRT
<213> ORGANISM: artificial
<220> FEATURE:
<223> OTHER INFORMATION: Complementarity determining region

<400> SEQUENCE: 20

Glu Gly Ile Pro Asp Tyr
1               5

<210> SEQ ID NO 21
<211> LENGTH: 16
<212> TYPE: PRT
<213> ORGANISM: artificial
<220> FEATURE:
<223> OTHER INFORMATION: Complementarity determining region

<400> SEQUENCE: 21

Lys Ser Ser Gln Ser Leu Leu Tyr Ser Asn Gly Lys Thr Tyr Leu Asn
1               5                   10                  15

<210> SEQ ID NO 22
<211> LENGTH: 7
<212> TYPE: PRT
```

<213> ORGANISM: artificial
<220> FEATURE:
<223> OTHER INFORMATION: Complementarity determining region

<400> SEQUENCE: 22

Val Val Ser Lys Leu Asp Ser
1               5

<210> SEQ ID NO 23
<211> LENGTH: 9
<212> TYPE: PRT
<213> ORGANISM: artificial
<220> FEATURE:
<223> OTHER INFORMATION: Complementarity determining region

<400> SEQUENCE: 23

Val Gln Gly Thr His Tyr Pro Phe Thr
1               5

<210> SEQ ID NO 24
<211> LENGTH: 342
<212> TYPE: DNA
<213> ORGANISM: artificial
<220> FEATURE:
<223> OTHER INFORMATION: antibody variable region

<400> SEQUENCE: 24
gaagtgaagc ttgaggagtc tggaggaggc ttggtgcaac ctggaggatc catgaaactc      60
tcgtgtactg cctctggact cactcttagt gacgcctgga tgaactgggt ccgccagtct     120
ccagagaagg ggcttgagtg ggttgctgaa attagaagca aagcttataa gcatgcaaca     180
tactatgctg agtctgtgaa aggcaggttc accatctcaa gagatgattc caaaagttgt     240
atctacctgc aaatgaacac cttaagagct gaggacactg gcattattat ctgtaccaga     300
catggttctt ggggcccagg gactctggtc actgtctctg ca                       342

<210> SEQ ID NO 25
<211> LENGTH: 114
<212> TYPE: PRT
<213> ORGANISM: artificial
<220> FEATURE:
<223> OTHER INFORMATION: antibody variable region

<400> SEQUENCE: 25

Glu Val Lys Leu Glu Glu Ser Gly Gly Gly Leu Val Gln Pro Gly Gly
1               5                   10                  15

Ser Met Lys Leu Ser Cys Thr Ala Ser Gly Leu Thr Leu Ser Asp Ala
            20                  25                  30

Trp Met Asn Trp Val Arg Gln Ser Pro Glu Lys Gly Leu Glu Trp Val
        35                  40                  45

Ala Glu Ile Arg Ser Lys Ala Tyr Lys His Ala Thr Tyr Tyr Ala Glu
    50                  55                  60

Ser Val Lys Gly Arg Phe Thr Ile Ser Arg Asp Asp Ser Lys Ser Cys
65                  70                  75                  80

Ile Tyr Leu Gln Met Asn Thr Leu Arg Ala Glu Asp Thr Gly Ile Tyr
                85                  90                  95

Tyr Cys Thr Arg His Gly Ser Trp Gly Pro Gly Thr Leu Val Thr Val
                100                 105                 110

Ser Ala

<210> SEQ ID NO 26

<211> LENGTH: 321
<212> TYPE: DNA
<213> ORGANISM: artificial
<220> FEATURE:
<223> OTHER INFORMATION: antibody variable region

<400> SEQUENCE: 26

```
gacatcctga tgtcccaatc tccatcctcc atgtctgttt ctctgggaga cagagtcagc    60
atcacttgcc gtgcaagtca gggaattagt agtaaaatgg ggtggttgca gcagaaacca   120
gggaaatcat ctaagggcct gatctatcat ggaaccaagt tggaagatgg agttccatcg   180
aggttcagtg gcagtggatc tggagcagaa tattctctca ccatcagtag cctggaatct   240
gaggattttg gagactatta ctgtgtacag tatgctcagt ttccgtacac gttcggaggg   300
gggaccaagc tggaaataaa a                                             321
```

<210> SEQ ID NO 27
<211> LENGTH: 107
<212> TYPE: PRT
<213> ORGANISM: artificial
<220> FEATURE:
<223> OTHER INFORMATION: antibody variable region

<400> SEQUENCE: 27

```
Asp Ile Leu Met Ser Gln Ser Pro Ser Ser Met Ser Val Ser Leu Gly
1               5                   10                  15
Asp Arg Val Ser Ile Thr Cys Arg Ala Ser Gln Gly Ile Ser Ser Lys
            20                  25                  30
Met Gly Trp Leu Gln Gln Lys Pro Gly Lys Ser Ser Lys Gly Leu Ile
        35                  40                  45
Tyr His Gly Thr Lys Leu Glu Asp Gly Val Pro Ser Arg Phe Ser Gly
    50                  55                  60
Ser Gly Ser Gly Ala Glu Tyr Ser Leu Thr Ile Ser Ser Leu Glu Ser
65                  70                  75                  80
Glu Asp Phe Gly Asp Tyr Tyr Cys Val Gln Tyr Ala Gln Phe Pro Tyr
                85                  90                  95
Thr Phe Gly Gly Gly Thr Lys Leu Glu Ile Lys
            100                 105
```

<210> SEQ ID NO 28
<211> LENGTH: 346
<212> TYPE: DNA
<213> ORGANISM: artificial
<220> FEATURE:
<223> OTHER INFORMATION: antibody variable region

<400> SEQUENCE: 28

```
gagtgaagtg aaacttgagg agtctggagg aggcttggta caacctggag gatccatgaa    60
actctcttgt actgcctctg gaatcactct taatgacgcc tggatgacct gggtccgcca   120
gtctccagag aagggccttg agtggggttgg tgaaattaga acaaagcta ataatcatgc   180
aacaaactat gctgagtctg tgaaagggag gttcagcatc tcaagagatg attccaaagg   240
tattgtctac ctgcaaatga atagcttaag agctgaagac actggcaatt attactgtac   300
caggcattct tactgggccc agggactct ggtcactgtc tctgca                   346
```

<210> SEQ ID NO 29
<211> LENGTH: 114
<212> TYPE: PRT
<213> ORGANISM: artificial
<220> FEATURE:

<223> OTHER INFORMATION: antibody variable region

<400> SEQUENCE: 29

Glu Val Lys Leu Glu Glu Ser Gly Gly Gly Leu Val Gln Pro Gly Gly
1               5                   10                  15

Ser Met Lys Leu Ser Cys Thr Ala Ser Gly Ile Thr Leu Asn Asp Ala
            20                  25                  30

Trp Met Thr Trp Val Arg Gln Ser Pro Glu Lys Gly Leu Glu Trp Val
        35                  40                  45

Gly Glu Ile Arg Asn Lys Ala Asn Asn His Ala Thr Asn Tyr Ala Glu
    50                  55                  60

Ser Val Lys Gly Arg Phe Ser Ile Ser Arg Asp Asp Ser Lys Gly Ile
65                  70                  75                  80

Val Tyr Leu Gln Met Asn Ser Leu Arg Ala Glu Asp Thr Gly Asn Tyr
                85                  90                  95

Tyr Cys Thr Arg His Ser Tyr Trp Gly Pro Gly Thr Leu Val Thr Val
            100                 105                 110

Ser Ala

<210> SEQ ID NO 30
<211> LENGTH: 321
<212> TYPE: DNA
<213> ORGANISM: artificial
<220> FEATURE:
<223> OTHER INFORMATION: antibody variable region

<400> SEQUENCE: 30
gacatcctga tgacccaatc tccatcctcc atgtctgtat ctctgggaga cacagtcagc      60
atcacgtgcc atgcaagtca gggcattaga aataatatag gtggttgca ggagaaacca      120 gggaaatcat ttaagggcct gatctatcat ggaaccaagt tggaagatgg aattccatca     180
aggttcagtg gcagtggatc tggagcagat tattctctca ccatcagtag cctggaatct    240
gaagatgttg cagactatta ctgtgtacaa tatgatcagt ttccgtacac gttcggaggg    300
gggaccaagc tggaaataaa a                                               321

<210> SEQ ID NO 31
<211> LENGTH: 107
<212> TYPE: PRT
<213> ORGANISM: artificial
<220> FEATURE:
<223> OTHER INFORMATION: antibody variable region

<400> SEQUENCE: 31

Asp Ile Leu Met Thr Gln Ser Pro Ser Ser Met Ser Val Ser Leu Gly
1               5                   10                  15

Asp Thr Val Ser Ile Thr Cys His Ala Ser Gln Gly Ile Arg Asn Asn
            20                  25                  30

Ile Gly Trp Leu Gln Glu Lys Pro Gly Lys Ser Phe Lys Gly Leu Ile
        35                  40                  45

Tyr His Gly Thr Lys Leu Glu Asp Gly Ile Pro Ser Arg Phe Ser Gly
    50                  55                  60

Ser Gly Ser Gly Ala Asp Tyr Ser Leu Thr Ile Ser Ser Leu Glu Ser
65                  70                  75                  80

Glu Asp Val Ala Asp Tyr Tyr Cys Val Gln Tyr Asp Gln Phe Pro Tyr
                85                  90                  95

Thr Phe Gly Gly Gly Thr Lys Leu Glu Ile Lys
            100                 105

<210> SEQ ID NO 32
<211> LENGTH: 10
<212> TYPE: PRT
<213> ORGANISM: artificial
<220> FEATURE:
<223> OTHER INFORMATION: Complementarity determining region

<400> SEQUENCE: 32

Gly Leu Thr Leu Ser Asp Ala Trp Met Asn
1               5                   10

<210> SEQ ID NO 33
<211> LENGTH: 19
<212> TYPE: PRT
<213> ORGANISM: artificial
<220> FEATURE:
<223> OTHER INFORMATION: Complementarity determining region

<400> SEQUENCE: 33

Glu Ile Arg Ser Lys Ala Tyr Lys His Ala Thr Tyr Tyr Ala Glu Ser
1               5                   10                  15

Val Lys Gly

<210> SEQ ID NO 34
<211> LENGTH: 3
<212> TYPE: PRT
<213> ORGANISM: artificial
<220> FEATURE:
<223> OTHER INFORMATION: Complementarity determining region

<400> SEQUENCE: 34

His Gly Ser
1

<210> SEQ ID NO 35
<211> LENGTH: 11
<212> TYPE: PRT
<213> ORGANISM: artificial
<220> FEATURE:
<223> OTHER INFORMATION: Complementarity determining region

<400> SEQUENCE: 35

Arg Ala Ser Gln Gly Ile Ser Ser Lys Met Gly
1               5                   10

<210> SEQ ID NO 36
<211> LENGTH: 7
<212> TYPE: PRT
<213> ORGANISM: artificial
<220> FEATURE:
<223> OTHER INFORMATION: Complementarity determining region

<400> SEQUENCE: 36

His Gly Thr Lys Leu Glu Asp
1               5

<210> SEQ ID NO 37
<211> LENGTH: 9
<212> TYPE: PRT
<213> ORGANISM: artificial
<220> FEATURE:
<223> OTHER INFORMATION: Complementarity determining region

<400> SEQUENCE: 37

Val Gln Tyr Ala Gln Phe Pro Tyr Thr

<210> SEQ ID NO 38
<211> LENGTH: 10
<212> TYPE: PRT
<213> ORGANISM: artificial
<220> FEATURE:
<223> OTHER INFORMATION: Complementarity determining region

<400> SEQUENCE: 38

Gly Ile Thr Leu Asn Asp Ala Trp Met Thr
1               5                   10

<210> SEQ ID NO 39
<211> LENGTH: 19
<212> TYPE: PRT
<213> ORGANISM: artificial
<220> FEATURE:
<223> OTHER INFORMATION: Complementarity determining region

<400> SEQUENCE: 39

Glu Ile Arg Asn Lys Ala Asn Asn His Ala Thr Asn Tyr Ala Glu Ser
1               5                   10                  15

Val Lys Gly

<210> SEQ ID NO 40
<211> LENGTH: 3
<212> TYPE: PRT
<213> ORGANISM: artificial
<220> FEATURE:
<223> OTHER INFORMATION: Complementarity determining region

<400> SEQUENCE: 40

His Ser Tyr
1

<210> SEQ ID NO 41
<211> LENGTH: 11
<212> TYPE: PRT
<213> ORGANISM: artificial
<220> FEATURE:
<223> OTHER INFORMATION: Complementarity determining region

<400> SEQUENCE: 41

His Ala Ser Gln Gly Ile Arg Asn Asn Ile Gly
1               5                   10

<210> SEQ ID NO 42
<211> LENGTH: 7
<212> TYPE: PRT
<213> ORGANISM: artificial
<220> FEATURE:
<223> OTHER INFORMATION: Complementarity determining region

<400> SEQUENCE: 42

His Gly Thr Lys Leu Glu Asp
1               5

<210> SEQ ID NO 43
<211> LENGTH: 9
<212> TYPE: PRT
<213> ORGANISM: artificial
<220> FEATURE:
<223> OTHER INFORMATION: Complementarity determining region

<400> SEQUENCE: 43

Val Gln Tyr Asp Gln Phe Pro Tyr Thr
1               5

<210> SEQ ID NO 44
<211> LENGTH: 10
<212> TYPE: PRT
<213> ORGANISM: artificial
<220> FEATURE:
<223> OTHER INFORMATION: antibody variable region
<220> FEATURE:
<221> NAME/KEY: Mutagen
<222> LOCATION: (9)..(9)
<223> OTHER INFORMATION: Xaa in position 9 can be I or L

<400> SEQUENCE: 44

Gly Tyr Thr Phe Thr Asp Tyr Tyr Xaa Asn
1               5                   10

<210> SEQ ID NO 45
<211> LENGTH: 17
<212> TYPE: PRT
<213> ORGANISM: artificial
<220> FEATURE:
<223> OTHER INFORMATION: antibody variable region
<220> FEATURE:
<221> NAME/KEY: Mutagen
<222> LOCATION: (2)..(2)
<223> OTHER INFORMATION: Xaa in position 2 may be I or L
<220> FEATURE:
<221> NAME/KEY: Mutagen
<222> LOCATION: (3)..(3)
<223> OTHER INFORMATION: Xaa in position 3 may be Y or N
<220> FEATURE:
<221> NAME/KEY: Mutagen
<222> LOCATION: (9)..(9)
<223> OTHER INFORMATION: Xaa in position 9  may be V or T

<400> SEQUENCE: 45

Trp Xaa Xaa Pro Gly Ser Gly Asn Xaa Lys Tyr Asn Glu Lys Phe Lys
1               5                   10                  15
Gly

<210> SEQ ID NO 46
<211> LENGTH: 6
<212> TYPE: PRT
<213> ORGANISM: artificial
<220> FEATURE:
<223> OTHER INFORMATION: antibody variable region
<220> FEATURE:
<221> NAME/KEY: Mutagen
<222> LOCATION: (3)..(3)
<223> OTHER INFORMATION: Xaa in position 3 may be I or L
<220> FEATURE:
<221> NAME/KEY: Mutagen
<222> LOCATION: (4)..(4)
<223> OTHER INFORMATION: Xaa in position 4 may be I or P
<220> FEATURE:
<221> NAME/KEY: Mutagen
<222> LOCATION: (5)..(5)
<223> OTHER INFORMATION: Xaa in position 5 may be V or D

<400> SEQUENCE: 46

Glu Gly Xaa Xaa Xaa Tyr
1               5

<210> SEQ ID NO 47
<211> LENGTH: 16
<212> TYPE: PRT
<213> ORGANISM: artificial
<220> FEATURE:
<223> OTHER INFORMATION: antibody variable region

```
<220> FEATURE:
<221> NAME/KEY: Mutagen
<222> LOCATION: (8)..(8)
<223> OTHER INFORMATION: Xaa in position 8 may be H or Y
<220> FEATURE:
<221> NAME/KEY: Mutagen
<222> LOCATION: (12)..(12)
<223> OTHER INFORMATION: Xaa in position 12 may be E or K
<220> FEATURE:
<221> NAME/KEY: Mutagen
<222> LOCATION: (13)..(13)
<223> OTHER INFORMATION: Xaa in position 13 may be T or S

<400> SEQUENCE: 47

Lys Ser Ser Gln Ser Leu Leu Xaa Ser Asn Gly Xaa Xaa Tyr Leu Asn
1               5                   10                  15

<210> SEQ ID NO 48
<211> LENGTH: 7
<212> TYPE: PRT
<213> ORGANISM: artificial
<220> FEATURE:
<223> OTHER INFORMATION: antibody variable region
<220> FEATURE:
<221> NAME/KEY: Mutagen
<222> LOCATION: (1)..(1)
<223> OTHER INFORMATION: Xaa in position 1 may be A or V

<400> SEQUENCE: 48

Xaa Val Ser Lys Leu Asp Ser
1               5

<210> SEQ ID NO 49
<211> LENGTH: 9
<212> TYPE: PRT
<213> ORGANISM: artificial
<220> FEATURE:
<223> OTHER INFORMATION: antibody variable region
<220> FEATURE:
<221> NAME/KEY: Mutagen
<222> LOCATION: (6)..(6)
<223> OTHER INFORMATION: Xaa in position 6 may be Y or F

<400> SEQUENCE: 49

Val Gln Gly Thr His Xaa Pro Phe Thr
1               5

<210> SEQ ID NO 50
<211> LENGTH: 10
<212> TYPE: PRT
<213> ORGANISM: artificial
<220> FEATURE:
<223> OTHER INFORMATION: antibody variable region
<220> FEATURE:
<221> NAME/KEY: Mutagen
<222> LOCATION: (2)..(2)
<223> OTHER INFORMATION: Xaa in position 2 may be I or L
<220> FEATURE:
<221> NAME/KEY: Mutagen
<222> LOCATION: (5)..(5)
<223> OTHER INFORMATION: Xaa in position 5 may be S or N
<220> FEATURE:
<221> NAME/KEY: Mutagen
<222> LOCATION: (10)..(10)
<223> OTHER INFORMATION: Xaa in position 10 may be N or T

<400> SEQUENCE: 50

Gly Xaa Thr Leu Xaa Asp Ala Trp Met Xaa
1               5                   10

<210> SEQ ID NO 51
```

```
<211> LENGTH: 19
<212> TYPE: PRT
<213> ORGANISM: artificial
<220> FEATURE:
<223> OTHER INFORMATION: antibody variable region
<220> FEATURE:
<221> NAME/KEY: Mutagen
<222> LOCATION: (4)..(4)
<223> OTHER INFORMATION: Xaa in position 4 may be S or N
<220> FEATURE:
<221> NAME/KEY: Mutagen
<222> LOCATION: (7)..(7)
<223> OTHER INFORMATION: Xaa in position 7 may be Y or N
<220> FEATURE:
<221> NAME/KEY: Mutagen
<222> LOCATION: (8)..(8)
<223> OTHER INFORMATION: Xaa in position 8 may be K or N
<220> FEATURE:
<221> NAME/KEY: Mutagen
<222> LOCATION: (12)..(12)
<223> OTHER INFORMATION: Xaa in position 12 Y or N

<400> SEQUENCE: 51

Glu Ile Arg Xaa Lys Ala Xaa Xaa His Ala Thr Xaa Tyr Ala Glu Ser
1               5                   10                  15

Val Lys Gly

<210> SEQ ID NO 52
<211> LENGTH: 3
<212> TYPE: PRT
<213> ORGANISM: artificial
<220> FEATURE:
<223> OTHER INFORMATION: antibody variable region
<220> FEATURE:
<221> NAME/KEY: Mutagen
<222> LOCATION: (2)..(2)
<223> OTHER INFORMATION: Xaa in position 2 may be G or S
<220> FEATURE:
<221> NAME/KEY: Mutagen
<222> LOCATION: (3)..(3)
<223> OTHER INFORMATION: Xaa in position 3 may be S or Y

<400> SEQUENCE: 52

His Xaa Xaa
1

<210> SEQ ID NO 53
<211> LENGTH: 11
<212> TYPE: PRT
<213> ORGANISM: artificial
<220> FEATURE:
<223> OTHER INFORMATION: antibody variable region
<220> FEATURE:
<221> NAME/KEY: Mutagen
<222> LOCATION: (1)..(1)
<223> OTHER INFORMATION: Xaa  in position 1 may be R or H
<220> FEATURE:
<221> NAME/KEY: Mutagen
<222> LOCATION: (7)..(7)
<223> OTHER INFORMATION: Xaa in position 7 may be S or R
<220> FEATURE:
<221> NAME/KEY: Mutagen
<222> LOCATION: (8)..(8)
<223> OTHER INFORMATION: Xaa in position 8 may be S or N
<220> FEATURE:
<221> NAME/KEY: Mutagen
<222> LOCATION: (9)..(9)
<223> OTHER INFORMATION: Xaa in position 9 may be K or N
<220> FEATURE:
<221> NAME/KEY: Mutagen
<222> LOCATION: (10)..(10)
<223> OTHER INFORMATION: Xaa in position 10 may be M or I

<400> SEQUENCE: 53
```

```
Xaa Ala Ser Gln Gly Ile Xaa Xaa Xaa Xaa Gly
1               5                   10

<210> SEQ ID NO 54
<211> LENGTH: 7
<212> TYPE: PRT
<213> ORGANISM: artificial
<220> FEATURE:
<223> OTHER INFORMATION: antibody variable region

<400> SEQUENCE: 54

His Gly Thr Lys Leu Glu Asp
1               5

<210> SEQ ID NO 55
<211> LENGTH: 9
<212> TYPE: PRT
<213> ORGANISM: artificial
<220> FEATURE:
<223> OTHER INFORMATION: antibody variable region
<220> FEATURE:
<221> NAME/KEY: Mutagen
<222> LOCATION: (4)..(4)
<223> OTHER INFORMATION: Xaa in position 4 may be A or D

<400> SEQUENCE: 55

Val Gln Tyr Xaa Gln Phe Pro Tyr Thr
1               5

<210> SEQ ID NO 56
<211> LENGTH: 10
<212> TYPE: PRT
<213> ORGANISM: Artificial Sequence
<220> FEATURE:
<223> OTHER INFORMATION: Complementarity determining region
<220> FEATURE:
<221> NAME/KEY: MUTAGEN
<222> LOCATION: (9)..(9)
<223> OTHER INFORMATION: any natural amino acid

<400> SEQUENCE: 56

Gly Tyr Thr Phe Thr Asp Tyr Tyr Xaa Asn
1               5                   10

<210> SEQ ID NO 57
<211> LENGTH: 17
<212> TYPE: PRT
<213> ORGANISM: Artificial Sequence
<220> FEATURE:
<223> OTHER INFORMATION: Complementarity determining region
<220> FEATURE:
<221> NAME/KEY: MUTAGEN
<222> LOCATION: (2)..(3)
<223> OTHER INFORMATION: any natural amino acid
<220> FEATURE:
<221> NAME/KEY: MUTAGEN
<222> LOCATION: (9)..(9)
<223> OTHER INFORMATION: any natural amino acid

<400> SEQUENCE: 57

Trp Xaa Xaa Pro Gly Ser Gly Asn Xaa Lys Tyr Asn Glu Lys Phe Lys
1               5                   10                  15

Gly

<210> SEQ ID NO 58
<211> LENGTH: 6
<212> TYPE: PRT
<213> ORGANISM: Artificial Sequence
```

<220> FEATURE:
<223> OTHER INFORMATION: Complementarity determining region
<220> FEATURE:
<221> NAME/KEY: MUTAGEN
<222> LOCATION: (3)..(5)
<223> OTHER INFORMATION: any natural amino acid

<400> SEQUENCE: 58

Glu Gly Xaa Xaa Xaa Tyr
1               5

<210> SEQ ID NO 59
<211> LENGTH: 16
<212> TYPE: PRT
<213> ORGANISM: Artificial Sequence
<220> FEATURE:
<223> OTHER INFORMATION: Complementarity determining region
<220> FEATURE:
<221> NAME/KEY: MUTAGEN
<222> LOCATION: (8)..(8)
<223> OTHER INFORMATION: any natural amino acid
<220> FEATURE:
<221> NAME/KEY: MUTAGEN
<222> LOCATION: (12)..(13)
<223> OTHER INFORMATION: any natural amino acid

<400> SEQUENCE: 59

Lys Ser Ser Gln Ser Leu Leu Xaa Ser Asn Gly Xaa Xaa Tyr Leu Asn
1               5                   10                  15

<210> SEQ ID NO 60
<211> LENGTH: 7
<212> TYPE: PRT
<213> ORGANISM: Artificial Sequence
<220> FEATURE:
<223> OTHER INFORMATION: Complementarity determining region
<220> FEATURE:
<221> NAME/KEY: MUTAGEN
<222> LOCATION: (1)..(1)
<223> OTHER INFORMATION: any natural amino acid

<400> SEQUENCE: 60

Xaa Val Ser Lys Leu Asp Ser
1               5

<210> SEQ ID NO 61
<211> LENGTH: 9
<212> TYPE: PRT
<213> ORGANISM: Artificial Sequence
<220> FEATURE:
<223> OTHER INFORMATION: Complementarity determining region
<220> FEATURE:
<221> NAME/KEY: MUTAGEN
<222> LOCATION: (6)..(6)
<223> OTHER INFORMATION: any natural amino acid

<400> SEQUENCE: 61

Val Gln Gly Thr His Xaa Pro Phe Thr
1               5

<210> SEQ ID NO 62
<211> LENGTH: 10
<212> TYPE: PRT
<213> ORGANISM: Artificial Sequence
<220> FEATURE:
<223> OTHER INFORMATION: Complementarity determining region
<220> FEATURE:
<221> NAME/KEY: MUTAGEN
<222> LOCATION: (2)..(2)
<223> OTHER INFORMATION: any natural amino acid
<220> FEATURE:

```
<221> NAME/KEY: MUTAGEN
<222> LOCATION: (5)..(5)
<223> OTHER INFORMATION: any natural amino acid
<220> FEATURE:
<221> NAME/KEY: MUTAGEN
<222> LOCATION: (10)..(10)
<223> OTHER INFORMATION: any natural amino acid

<400> SEQUENCE: 62

Gly Xaa Thr Leu Xaa Asp Ala Trp Met Xaa
1               5                   10

<210> SEQ ID NO 63
<211> LENGTH: 19
<212> TYPE: PRT
<213> ORGANISM: Artificial Sequence
<220> FEATURE:
<223> OTHER INFORMATION: Complementarity determining region
<220> FEATURE:
<221> NAME/KEY: MUTAGEN
<222> LOCATION: (4)..(4)
<223> OTHER INFORMATION: any natural amino acid
<220> FEATURE:
<221> NAME/KEY: MUTAGEN
<222> LOCATION: (7)..(8)
<223> OTHER INFORMATION: any natural amino acid
<220> FEATURE:
<221> NAME/KEY: MUTAGEN
<222> LOCATION: (12)..(12)
<223> OTHER INFORMATION: any natural amino acid

<400> SEQUENCE: 63

Glu Ile Arg Xaa Lys Ala Xaa Xaa His Ala Thr Xaa Tyr Ala Glu Ser
1               5                   10                  15

Val Lys Gly

<210> SEQ ID NO 64
<211> LENGTH: 3
<212> TYPE: PRT
<213> ORGANISM: Artificial Sequence
<220> FEATURE:
<223> OTHER INFORMATION: Complementarity determining region
<220> FEATURE:
<221> NAME/KEY: MUTAGEN
<222> LOCATION: (2)..(3)
<223> OTHER INFORMATION: any natural amino acid

<400> SEQUENCE: 64

His Xaa Xaa
1

<210> SEQ ID NO 65
<211> LENGTH: 11
<212> TYPE: PRT
<213> ORGANISM: Artificial Sequence
<220> FEATURE:
<223> OTHER INFORMATION: Complementarity determining region
<220> FEATURE:
<221> NAME/KEY: MUTAGEN
<222> LOCATION: (1)..(1)
<223> OTHER INFORMATION: any natural amino acid
<220> FEATURE:
<221> NAME/KEY: MUTAGEN
<222> LOCATION: (7)..(10)
<223> OTHER INFORMATION: any natural amino acid

<400> SEQUENCE: 65

Xaa Ala Ser Gln Gly Ile Xaa Xaa Xaa Xaa Gly
1               5                   10
```

```
<210> SEQ ID NO 66
<211> LENGTH: 9
<212> TYPE: PRT
<213> ORGANISM: Artificial Sequence
<220> FEATURE:
<223> OTHER INFORMATION: Complementarity determining region
<220> FEATURE:
<221> NAME/KEY: MUTAGEN
<222> LOCATION: (4)..(4)
<223> OTHER INFORMATION: any natural amino acid

<400> SEQUENCE: 66

Val Gln Tyr Xaa Gln Phe Pro Tyr Thr
1               5

<210> SEQ ID NO 67
<211> LENGTH: 9
<212> TYPE: PRT
<213> ORGANISM: murine
<220> FEATURE:
<221> NAME/KEY: MISC_FEATURE
<222> LOCATION: (1)..(1)
<223> OTHER INFORMATION: E in position 1 is pyrrolidone carboxylic acid

<400> SEQUENCE: 67

Glu Phe Arg His Asp Ser Gly Tyr Glu
1               5

<210> SEQ ID NO 68
<211> LENGTH: 9
<212> TYPE: PRT
<213> ORGANISM: murine
<220> FEATURE:
<221> NAME/KEY: MISC_FEATURE
<222> LOCATION: (1)..(1)
<223> OTHER INFORMATION: E in position 1 is pyrrolidone carboxylic acid

<400> SEQUENCE: 68

Glu Phe Gly His Asp Ser Gly Phe Glu
1               5
```